US008895557B2

(12) United States Patent
Beijnen et al.

(10) Patent No.: US 8,895,557 B2
(45) Date of Patent: Nov. 25, 2014

(54) PHARMACEUTICAL FORMULATIONS OF ECTEINASCIDIN COMPOUNDS

(75) Inventors: Jacob Hendrik Beijnen, Amsterdam (NL); Bastiaan Nuijen, Amsterdam (NL); Pilar Calvo Salve, Madrid (ES); Maria Tobio Barreira, Madrid (ES)

(73) Assignee: Pharma Mar, S.A., Sociedad Unipersonal, Madrid (ES)

( * ) Notice: Subject to any disclaimer, the term of this patent is extended or adjusted under 35 U.S.C. 154(b) by 801 days.

(21) Appl. No.: 11/261,876

(22) Filed: Oct. 28, 2005

(65) Prior Publication Data
US 2006/0094687 A1     May 4, 2006

Related U.S. Application Data

(60) Provisional application No. 60/623,813, filed on Oct. 29, 2004.

(51) Int. Cl.
| | | |
|---|---|---|
| A61K 31/50 | (2006.01) | |
| A61K 31/495 | (2006.01) | |
| A61K 31/715 | (2006.01) | |
| A61K 47/26 | (2006.01) | |
| A61K 47/18 | (2006.01) | |
| A61K 47/32 | (2006.01) | |
| A61K 47/02 | (2006.01) | |
| A61K 9/19 | (2006.01) | |
| A61K 31/498 | (2006.01) | |
| A61K 31/4995 | (2006.01) | |
| A61K 9/00 | (2006.01) | |

(52) U.S. Cl.
CPC ............. *A61K 31/4995* (2013.01); *A61K 47/26* (2013.01); *A61K 47/183* (2013.01); *A61K 47/32* (2013.01); *A61K 47/02* (2013.01); *A61K 9/19* (2013.01); *A61K 31/498* (2013.01); *A61K 9/0019* (2013.01)
USPC .............................. 514/249; 514/250; 514/53

(58) Field of Classification Search
USPC .................................................. 514/249, 250
See application file for complete search history.

(56) References Cited

U.S. PATENT DOCUMENTS

| | | | |
|---|---|---|---|
| 5,089,273 A | 2/1992 | Rinehart et al. | |
| 5,149,804 A | 9/1992 | Rinehart et al. | |
| 5,213,804 A | 5/1993 | Martin et al. | |
| 5,256,663 A | 10/1993 | Rinehart et al. | |
| 5,336,669 A * | 8/1994 | Palepu et al. | .................... 514/53 |
| 5,478,932 A | 12/1995 | Rinehart et al. | |
| 5,552,544 A | 9/1996 | Brana et al. | |
| 5,654,426 A | 8/1997 | Rinehart et al. | |
| 5,721,362 A | 2/1998 | Corey et al. | |
| 5,908,835 A | 6/1999 | Bissery | |
| 5,985,876 A | 11/1999 | Rinehart et al. | |
| 6,124,293 A | 9/2000 | Rinehart et al. | |
| 6,153,590 A | 11/2000 | Andersen et al. | |
| 6,348,467 B1 | 2/2002 | Corey | |
| 7,241,892 B1 | 7/2007 | Cuevas et al. | |
| 7,247,892 B2 | 7/2007 | Taylor | |
| 7,410,969 B2 | 8/2008 | Manzanares et al. | |
| 7,420,051 B2 | 9/2008 | Francesch | |
| 7,524,956 B2 | 4/2009 | Cuevas | |
| 7,622,458 B2 | 11/2009 | Rybak | |
| 2002/0137663 A1 | 9/2002 | Forman et al. | |
| 2002/0143038 A1 | 10/2002 | Bandyopadhyay et al. | |
| 2004/0002602 A1 | 1/2004 | Francesch et al. | |
| 2004/0019027 A1 * | 1/2004 | Forman et al. | ................. 514/179 |
| 2004/0067895 A1 * | 4/2004 | Faircloth et al. | ................. 514/28 |
| 2004/0108086 A1 | 6/2004 | Takahashi et al. | |
| 2005/0004018 A1 | 1/2005 | Jimeno | |
| 2006/0030571 A1 | 2/2006 | Rinehart | |
| 2006/0094687 A1 | 5/2006 | Beijnen | |
| 2007/0004691 A1 | 1/2007 | Donald | |
| 2007/0082856 A1 | 4/2007 | Gianni | |
| 2007/0128201 A1 | 6/2007 | D'Incalci et al. | |
| 2007/0275942 A1 | 11/2007 | Cvitkovich | |
| 2008/0076772 A1 | 3/2008 | Allavena | |
| 2008/0255132 A1 | 10/2008 | Rowinsky | |
| 2008/0293725 A1 | 11/2008 | Rosell Costa | |
| 2009/0117176 A1 | 5/2009 | Gilles | |
| 2009/0170860 A1 | 7/2009 | Scotto | |
| 2009/0324744 A1 | 12/2009 | Takahashi | |
| 2010/0009906 A1 | 1/2010 | Ali Elsayed | |

FOREIGN PATENT DOCUMENTS

| | | |
|---|---|---|
| CN | 1486193 | 3/2004 |
| JP | 5-501264 | 3/1993 |
| JP | 2000081438 | 3/2004 |
| WO | WO 91/05546 | 5/1991 |
| WO | WO 98/52598 | 11/1998 |
| WO | WO 99/51238 | 10/1999 |
| WO | WO 99/58125 | 11/1999 |
| WO | 00/69441 | 11/2000 |

(Continued)

OTHER PUBLICATIONS

Akers; "Excipient—Drug Interactions in Parenteral Formulations"; Journal of Pharmaceutical Sciences; Nov. 2002; 91(11): 2283-2300.*
Van Kesteren, Ch. et al. Anti-Cancer Drugs vol. 14, pp. 487-497. Published 2003.*
Faulkner et al., "Symbiotic Bacteria in Sponges: Sources of Bioactive Substances," Drugs from the Sea, Fusetani, N (ed.), Basel Karger, 2000, pp. 107-119.
Manzanares et al., "Advances in the Chemistry and Pharmacology of Ecteinascidins, A Promising New Class of Anticancer Agents," Curr. Med. Chem.—Anti-Cancer Agents, 2001, vol. 1, pp. 257-276.
Kovalcik et al., "The Stability of Cyclophosphamide in Lyophilized Cakes. part I. Mannitol, Lactose, and Sodium Biocarbonate as Excipients," Journal of Parenteral Science and Technology, vol. 42, No. 1, Jan.-Feb. 1988, pp. 29-37.

(Continued)

*Primary Examiner* — Paul Zarek
*Assistant Examiner* — George W Kosturko
(74) *Attorney, Agent, or Firm* — Kenneth H. Sonnenfeld; King & Spalding LLP

(57) ABSTRACT

Ecteinascidin formulations, methods of preparing the same, articles of manufacture and kits with such formulations, and methods of treating proliferative diseases with the same formulations are provided.

26 Claims, 5 Drawing Sheets

(56) References Cited

FOREIGN PATENT DOCUMENTS

Figure 1:
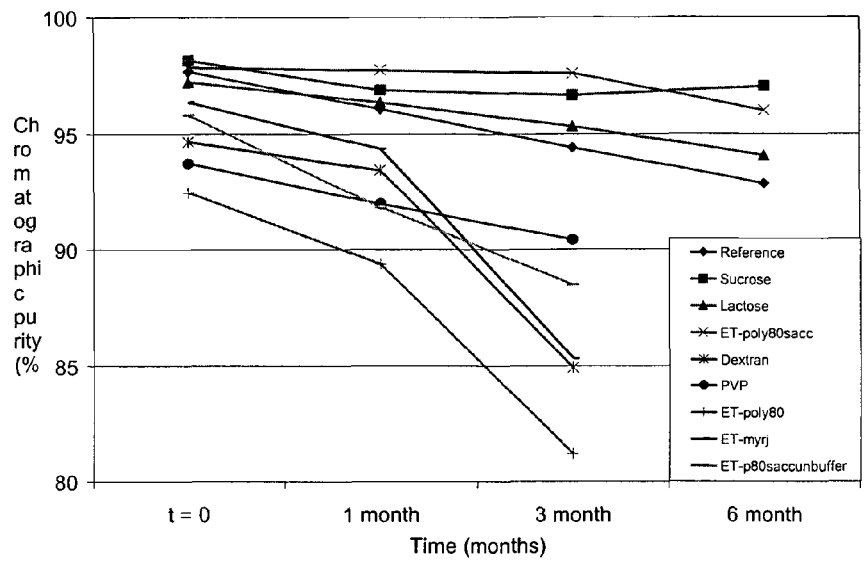

| WO | WO 00/69862 | 11/2000 | | |
|---|---|---|---|---|
| WO | 01/77115 | 10/2001 | | |
| WO | WO 01/77115 | 10/2001 | | |
| WO | WO 01/87894 | 11/2001 | | |
| WO | 02/36135 | 5/2002 | | |
| WO | 02/064843 | 8/2002 | | |
| WO | WO 02064843 A1 * | 8/2002 | | |
| WO | WO02064843 A1 * | 8/2002 | ........... | C07D 241/36 |
| WO | WO 02/78678 | 10/2002 | | |
| WO | WO 03/020259 | 3/2003 | | |
| WO | 03/039571 | 5/2003 | | |
| WO | WO 2005/049029 | 6/2005 | | |
| WO | WO 2005/049030 | 6/2005 | | |
| WO | WO 2005/049031 | 6/2005 | | |
| WO | WO 2006/035244 | 4/2006 | | |
| WO | WO 2006/046080 | 5/2006 | | |

OTHER PUBLICATIONS

Sakai et al., "Additional Antitumor Ecteinascidins from a Caribbean Tunicate: Crystal Structures and Activities in vivo," Proc. Natl. Acad. Sci., vol. 89, Dec. 1992, pp. 11456-11460.

van Kesteren et al., "Yondelis (trabectedin, ET-743): the Development of an Anticancer Agent of Marine Origin," Anti-Cancer Drugs, vol. 14, No. 7, 2003, pp. 487-502.

Menchaca et al., "Synthesis of Natural Ecteinascidins (ET-729, ET-745, ET-759B, ET-736, ET-637, ET-594) from Cyanosafracin B," J. Org. Chem., published on web Oct. 21, 2003, pp. 8859-8866.

U.S. Appl. No. 09/546,877, filed Apr. 10, 2000, Rinehart.
U.S. Appl. No. 09/787,461, filed Mar. 2, 2001, Cvitkovich et al.
U.S. Appl. No. 10/416,086, filed Sep. 17, 2003, Takahashi et al.
U.S. Appl. No. 10/492,320, filed Oct. 21, 2002, Jimeno et al.
U.S. Appl. No. 10/558,133, filed Nov. 23, 2005, D'Incalci et al.
U.S. Appl. No. 10/575,132, filed Apr. 7, 2006, Donald et al.
U.S. Appl. No. 10/579,130, filed May 12, 2006, Rowinsky et al.
U.S. Appl. No. 10/579,160, filed May 11, 2006, Rybek.
U.S. Appl. No. 10/579,251, filed Oct. 20, 2006, Gianni et al.
U.S. Appl. No. 11/132,466, filed May 18 2005, Rinehart et al.
U.S. Appl. No. 11/577,790, filed Apr. 23, 2007, Gilles et al.
U.S. Appl. No. 11/769,873, filed Jun. 28, 2007, Cvitkovich et al.

Akers, "Excipient—Drug Interactions in Parenteral Formulations," Journal of Pharmaceutical Sciences, 91(11), pp. 2283-2300, Nov. 2002.

Barrera, H. et al., "Interaction of ET-743 and standard cytotoxic agents against a panel of human tumor cell lines," Proceedings of the American Association for Cancer Research, vol. 40, p. 591, Abstract No. 3896, Mar. 1999.

Biroccio et al., "Telomere Dysfunction Increases Cisplatin and Ecteinascidin-743 Sensitivity of Melanoma Cells," Molecular Pharmacology, 63:632-638 (2003).

Blay et al., "Combination of Trabectedin and Doxorubicin for the Treatment of Patients with Soft Tissue Sarcoma: Safety and Efficacy Analysis," 43rd annual ASCO meeting, Jun. 1-5, 2007.

Bonfanti et al., "Effect ofEcteinascidin-743 on the Interaction Between DNA Binding Proteins and DNA." Anticancer Drug Des. 14, 179-86, 1999.

Bowman, A. et al., "Phase I clinical and pharmacokinetic (PK) study of ecteinascidin-743 (ET-743) given as a one hour infusion every 21 days," Annals Oncology, Abstract 452, 1998.

Brandon et al., In-vitro Cytotoxicity of ET-743 (Trabectedin, Yondelis), a Marine Anti-cancer Drug, in the Hep G2 Cell Line: Influence of Cytochrome P450 and Phase II Inhibition, and Cytochrome P450 Induction, Anti-cancer Drugs, 16:935-943 (2005).

European Agency for the Evaluation of Medicinal Products, "Committee for Proprietary Medicinal Products Summary of Opinion for Yondelis", Nov. 20, 2003.

Corey et al., "Enantioselective Total Synthesis of Ecteinascidin 743", J. Am. Chem. Soc., 118, 9202-9203, 1996.

Cvitkovic, E. et al., "Final results of a phase I study of ecteinascidin-743 (ET-743) 24 hour (h) continuous infusion (CI) in advanced solid tumors (AST) patients (pts)," 1999 ASCO Annual Meeting Proceedings, Abstract No. 690, May 15-18, 1999.

Cvitkovic, E. et al., "Ecteinascidin-743 (ET-743) 24 hour continuous intravenous infusion (CI) phase I study in solid tumors (ST) patients," Annals Oncology, Abstract 456, 1998.

Delaloge, S. et al., "Ecteinascidin-743: A Marine-Derived Compound in Advanced Pretreated Sarcoma Patients—Preliminary Evidence of Activity", J. of Clinical Oncology, vol. 19, No. 5, pp. 1248-1255, 2001.

DeVita et al., "Combination Versus Single Agent Chemotherapy: A Review of the Basis for Selection of Drug Treatment of Cancer", Cancer, vol. 35, pp. 98-110, 1975.

D'Incalci et al., "The Combination of ET-743 and Cisplatin (DDP): From a Molecular Pharmacology Study to a Phase I Clinical Trial," from the AACR Annual Meeting of Apr. 6-10, 2002, Abstract 404.

D'Incalci et al., "In human tumor xenografts the resistance to ET-743 or to cisplatin can be overcome by giving the two drugs in combination," European Journal of Cancer, 38, Suppl. 7, 34 (Nov. 2002).

D'Incalci et al., "Preclinical and Clinical Results with the Natural Marine Product ET-743," Expert Opin. Investig. Drugs, 12(11):1843-1853 (2003).

D'Incalci et al., "The combination of yondelis and cisplatin is synergistic against human tumor xenografts," European Journal of Cancer 39: 1920-1926 (2003).

Donald et al., "Complete Protection by High-Dose Dexamethasone Against the Hepatotoxicity of the Novel Antitumor Drug Yondelis (ET-743) in the Rat," Cancer Research, vol. 63, p. 5902-5908, Sep. 2003.

Donald et al ., "Dietary Agent Indole-3-Carbinol Protects Female Rats Against the Hepatotoxicity of the Antitumor Drug ET-743 (trabectidin) Without Compromising Efficacy in a Rat Mammary Carcinoma" International Journal of Cancer, vol. 111, No. 6, p. 961-967, 2004.

"Doxil (doxorubicin Hcl Liposome Injection) Product Information", Oct. 10, 2004, pp. 1-16, XP002389462, <<web.archive.org/web/20041009180>>.

Drugs Fut., "Ecteinascidin-743" vol. 22, No. 11, p. 1279, 1997.

Eckhardt et al., "In vitro Studies of a Novel Marine Cytotoxic, Ecteinascidin (ET-743)," New Drugs and Pharmacology, Annals of Oncology, 7 (Suppl. 5), 131, Abstract 632P (1996).

Endo et al., "Total Synthesis of Ecteinascidin 743", J. Am. Chem. Soc., 124, 6552-6554, 2002.

Erba et al., "Synergistic cytotoxic effect of ET-743 and cisplatin," Clinical Cancer Research, vol. 6, Abstract 209 (Nov. 2000).

Erba et al., "Combination of yondelis (ET-743) and oxaliplatin in experimental ovarian cancer," from the AACR-NCI-EORTC International Conference on Molecular Targets and Cancer Therapeutics of Nov. 17-21, 2003, Abstract C247.

Erba et al., "ET-743 and Cisplatin (DDP) Show in Vitro and in Vivo Synergy Against Human Sarcoma and Ovarian Carcinoma Cell Lines," from the AACR-NCI-EORTC Conference on Molecular Targets and Cancer Therapeutics of Oct. 29-Nov. 2, 2001, Abstract 406.

Erlichman, C., "18: Pharmacology of Anticancer Drugs," The Basic Science of Oncology, 2nd edition, Tannock et al., editors, McGraw-Hill, New York, pp. 317-337, 1992.

FDA approved label for Pharmacia and Upjohn's Doxorubicin Hydrochloride for Injection (May 8, 2003).

Faircloth et al., "In Vivo Combinations of Chemotherapeutic Agents with Ecteinascidin 743 (ET743) Against Solid Tumors," from the Proceedings AACR-NCI-EORTC of Nov. 2001, Abstract 387.

Faircloth et al., "Dexamethasone Potentiates the Activity of Ecteinascidin 743 in Preclinical Melanoma and Osteosarcoma Models," Abstract and Presentation 379 (2002).

Fayette et al., "ET-743: a Novel Agent with Activity in Soft-Tissue Sarcomas," Current Opinion in Oncology, 18:347-353 (2006).

Fourouzesh, B. et al., "Phase I and pharmacokinetic study of the marine-derived DNA minor groove binder ET-743 on a weekly x3 every-4-week schedule in patients with advanced solid malignancies," Proceedings of the 2001 AACR-NCI-EOTRC International Conference, Abstract No. 209, Oct. 29-Nov. 2, 2001.

(56) References Cited

OTHER PUBLICATIONS

Fourouzesh, B. et al., "Phase I and pharmacokinetic study of ET-743, a minor groove DNA binder, administrated weekly to patients with advanced cancer," Proc Am Soc Clin Oncol, vol. 20, 2001 ASCO Annual Meeting Proceedings, Abstract No. 373, 2001.

Forouzesh, B., et al., "Phase I and pharmacokinetic study of ET-743, a minor groove DNA binder, administered weekly to patients with advanced cancer," European Journal of Cancer, ECCO 11, vol. 37, supplement 6, Abstract No. 106, Oct. 21-25, 2001.

Fukuyama et al., "Total Synthesis of Saframycin A," J. Am. Chem. Soc., 112, 3712-3713, 1990.

Garcia Gravalos, M.D., et al., "In vitro schedule-dependent cytotoxicity by ecteinascidin 743 (ET-743) against human tumor cells," 23rd European Society for Medical Oncology Congress, Abstract No. 652, Nov. 6-10, 1998.

Ghielmini, M. et al., "Schedule-dependent myelotoxicity induced in vitro by the new marine derived minor groove interacting agent ecteinascidin 743," ECCO vol. 9, Abstract No. 807, Sep. 17, 1997.

Ghielmini, M. et al., "In vitro schedule-dependency of myelotoxicity and cytotoxicity of Ecteinascidin 743 (ET-743)," Annals of Oncology, vol. 9, pages.

Gianni et al. "Definition of the Least Toxic Sequence and Optimal Therapeutic Dose of Yondelis® in Combination with Doxorubicin in Patients with Untreated Metastatic Soft Tissue Sarcomas and Advanced Pre-Treated Anthracycline," Clinical Cancer Research, vol. 9, No. 16, p. 6081S (Dec. 2003).

Goodman & Gilman's The Pharmaceutical Basis of Therapeutics, p. 36, 1975.

Goodman & Gilman's The Pharmaceutical Basis of Therapeutics (9$^{th}$ edition), p. 930, 1996.

Goodman & Gilman's The Pharmaceutical Basis of Therapeutics (9$^{th}$ edition), pp. 1230. 1232, 1996.

Greyer et al., "The National Cancer Institute: Cancer Drug Discovery and Development Program", Seminars in Oncology, vol. 19, No. 6, 622-638, Dec. 1992.

Grosso et al., "Steroid Premedication Markedly Reduces Liver and Bone Marrow Toxicity of Trabectedin in Advanced Sarcoma," European Journal of Cancer 42:10, 1484-1490 (2006).

Gurtler, J.S. et al., "Trabectedin in third line breast cancer: a multicenter, randomized, phase II study comparing two administration regimens," Journal of Clinical Oncology, 2005 ASCO Annual Meeting Proceedings, vol. 23, No. 16S, part I of II (Jun. 1 Supplement), Abstract No. 625, 2005.

Hendriks, H.R. et al., "High antitumor activity of ET743 against human tumor xenografts from melanoma, non-small-cell lung and ovarian cancer," Annals of Oncology, vol. 10, pp. 1233-1240, 1999.

Hidalgo, M., et al., "A phase I and pharmacokinetic (PK) study of ET-743, a novel minor groove binder of marine origin administered on a daily × 5 schedule," 23rd European Society for Medical Oncology Congress, Abstract No. 613P, Nov. 6-10, 1998.

Hillebrand, M.J.X. et al., "Pharmacokinetics of ecteinascidin-743 (ET-743) in three phase I studies," Annals Oncology, Abstract No. 455, 1998.

Holmes, "Paclitaxel Combination Therapy in the treatment of Metast Breast Cancer: A Review," Seminars in Oncology, vol. 23, pp. 46-56, 1996.

Hornicek et al., "Effect of Ecteinascidin-743 and Plasminogen related Protein B on a Human Chondrosarcoma Xenograft Tumor in Mice," Clinical Cancer Research, vol. 7 Supplement P3734S-3734S, Abstract 398 (Nov. 2001).

Ishikawa et al., "Tumor Selective Delivery of 5-Fluorouracil by Capecitabine," Biochemical Pharmacology, vol. 55, pp. 1091-1097, 1998.

Izbicka, E. et al., "In vitro antitumor activity of the novel marine agent, Ecteinascidin-743 (ET-743, NSC-648766) against human tumors explanted from patients," Annals of Oncology, vol. 9, pp. 981-987, 1998.

Jimeno, J.M. et al., "Enhancing the preclinical in vivo antitumor activity of ecteinascidin 743, a marine natural product currently in phase II clinical trials," Proceedings of the 1999 AACR-NCI-EORTC International Conference, Clinical Cancer Reserach, vol. 5, Abstract No. 306, Nov. 1999.

Jimeno, J. et al., "Phase I and pharmacokinetic (PK) study of Et-743, a novel minor groove binder of marine origin on a daily [times] 5 schedule," 1998 ASCO Annual Meeting Proceedings, Abstract No. 737, 1998.

Jimeno, Jose et al., "Adding Pharmacogenomics to the Development of New Marine-Derived Anticancer Agents," Journal of Translational Medicine, vol. 4, issue 3, Jan. 9, 2006, downloaded from the internet website: <<http://www.translational-medicine.com/content/4/1/3>>.

Jin, et al., Ecteinascidin-743, A Transcription-Targeted Chemotherapeutic that Inhibits MDR I Activation. Proc. Natl. Acad. Sci. USA, 97, 6775-9, 2000.

Kanzaki et al., "Activity of Ecteinascidin 743 and Synergism with Doxorubicin and Vincristine in P-Glycoprotein/MDR1 Over-Expression Cell Lines," from the Proceedings of the AACR, vol. 42, Abstract 4354 (Mar. 2001).

Kanzaki et al., "Microsatellite Instability (MSI) Induced by Ecteinascidin743 and Protection with Aspirin," from the 93rd Annual Meeting of the American Association for Cancer Research, Abstract 5382 (Apr. 6-10, 2002).

Laverdiere et al., "Phase II Study of Ecteinascidin 743 in Heavily Pretreated Patients with Recurrent Osteosarcoma", Cancer, American Cancer Society, Philadelphia, PA, Aug. 15, 2003, vol. 98:4, pp. 832-840, XP002314512.

Leonetti et al., "Antitumoral Effect of the G-quadraplex Interactive Compound RHPS4 on Human Melanoma Cells Possessing Relatively Long Telomeres," from the Proceedings of the AACR, vol. 45, Mar. 2004.

Maier et al., "In vitro inhibition of endothelial cell growth by the antiangiogenic drug AGM-1470 (TNP-470) and the antiendoglin antibody TEC-11," Anti-Cancer Drugs, vol. 8, pp. 238-244, 1997.

Magro et all., "The Role of PARP and PARP Inhibitors in Yondelis (Trabectedin) Mediated Cytotoxicity," Abstract and Presentation from the AACR Annual Meeting, Apr. 17, 2007.

Martinez, et al., Phthalascidin, A Synthetic Antitumor Agent with Potency and Mode of Action Comparable to Eeteinaseidin 743. Proc. Natl. Acad. Sci. USA 96; 3496-501, 1999.

Martinez, E. J. et al., A New, More Efficient, and Effective Process for the Synthesis of a Key Pentacyclic Intermediate for Production of Ecteinascidin and Phthalascidin Antitumor Agents. Org. Lett. 2, 993-6, 2000.

McLeod, "Clinically relevant drug-drug interactions in oncology," Br. J. Clin. Pharmacol., 45:539-544 (1998).

McMeekin, D.S. et al., "Final results of a phase II study of weekly trabectedin in second/third line ovarian carcinoma," Journal of Clinical Oncology, 2005 ASCO Annual Meeting Proceedings, vol. 23, No. 16S, Part I of II (Jun. 1 Supplement), Abstract No. 501, May 13-17, 2005.

Meco et al., "Effective combination of ET-743 and doxorubicin in sarcoma: preclinical studies," Cancer Chemother. Pharmacol. 52: 131-138 (2003).

Meco et al., "The combination of ET-743 and Irinotecan is active in preclinical models in rhabomyosarcoma," presented at the 16th EORTC-NCI-AARC Symposium on Molecular Targets and Cancer Therapeutics held in Geneva on Sep. 28-Oct. 1, 2004.

Merck Manual on-line edition version, "Types: Overview of Cancer," 4 pages, downloaded from internet website <<http://www.merck.com/mmhe>>, Feb. 2003.

Michaelson, M.D. et al., "Phase II study of three hour, weekly infusion of trabectedin (ET-743) in men with metastatic, androgen-independent prostate carcinoma (AIPC)," Journal of Clinical Oncology, 2005 ASCO Annual Meeting Proceedings, vol. 23, No. 16S, Part I of II (Jun. 1 Supplement), Abstract No. 4517, May 13-17, 2005.

Minuzzo, M. et al., "Interference of Transcriptional Activation by the Antineoplastic Drug Ecteinascidin.743." Proc. Natl. Acad. Sci. USA 97, 6780-4, 2000.

Moore et al., "Sequencing evaluation of ET-743 combinations with standard chemotherapy agents against a panel of human tumor cell lines," Clinical Cancer Research, vol. 6, Abstract 504 (Nov. 2000).

(56) References Cited

OTHER PUBLICATIONS

Morioka et al., "Antiangiogenesis Treatment Combined with Chemotherapy Produces Chondrosarcoma Necrosis," Clinical Cancer Research, vol. 9, 1211-1217, Mar. 2003.
Pharma Mar Press Release, "PharmaMar Differs with CPMP Opinion", Pharma Mar Grupo Zeltia, <<http://www.pharmamar.com/en/press/news_release.cfm>>, Jul. 24, 2003.
Pharma Mar Press Release, "PharmaMar Receives EMEA Appeal Decision on Yondelis in Soft Tissue Sarcoma", Pharma Mar Grupo Zeltia, <<http://www.pharmamar.com/en/press/news_release.cfm>>, Nov. 20, 2003.
Pharma Mar Press Release, "Yondelis(r) STS-201 Efficacy and Safety Data Presented at ASCO 2007" Pharma Mar Grupo Zeltia, <<http://www.pharmamar.com/en/press>>, Jun. 5, 2007.
Pharma Mar Press Release, "The European Commission Authorizes Yondelis(r) Commericalization for Soft Tissue Sarcoma" Pharma Mar Grupo Zeltia, <<http://www.pharmamar.com/en/press>>, Sep. 20, 2007.
Pommier, et al., "DNA Sequence- and Structure-Selective Alkylation of Guanine N2 in the DNA Minor Groove by Ecteinascidin 743, a Potent Antitut:l1or Compound from the Caribbean Tunicate *Ecteinascidia turbinata*." Biochemistry 35, 13303-9, 1996.
Rinehart, K.L., "Antitumor Compounds from Tunicates." Moo. Res. Rev. 20, 1-27, 2000.
Riccardi et al., "Preclinical Activity and Biodistribution of Ecteinascidin 743 (ET-743) and Doxorubicin (DOX) Combinations in Human Rhabdomyosarcoma," from the AACR-NCI-EORTC Conference on Molecular Targets and Cancer Therapeutics of Oct. 29-Nov. 2, 2001, Abstract 405.
Riccardi et al., "Effective Combinations of ET-743 and Doxorubicin for Tumor Growth Inhibitions Against Murine and Human Sarcomas in Athymic Mice," from the Proceedings of the AACR, vol. 42, Abstract 1132 (Mar. 2001).
Riccardi et al., "Combination of trabectedin and irinotecan is highly effective in a human rhabdomyosarcoma xenograft," Anti-Cancer Drugs, 16:811-815 (2005).
Riofrio, M. et al., "Ecteinascidin-743 (ET-743) 24 hours continuous infusion (CI): Clinical and pharmacokinetic phase I study progressive report," 23rd European Society for Medical Congress, Abstract 639P, Nov. 6-10, 1998.
Robert et al.,"Pharmacokinetics of Doxorubicin in Sarcoma Patients," Eur. J. Clin. Pharmcol., vol. 31, pp. 695-699, 1987.
Ryan, DP et al., "Phase I and Pharmacokinetic Study of Ecteinascidin-743 Administered as a 72 hours Continuous Intravenous Infusion in Patients with Solid Malignancies", Clinical Cancer Research, vol. 7, pp. 231-242, 2001.
Saito et al.,"Synthesis of Saframycins-3," J. Org. Chem., 54, 5391, 1989.
Sato et al., "Multicenter Phase II Trial of Weekly Paclitazel for Advanced or Metastatic Breast Cancer: the Saitama Breast Cancer Clincal Study Group (SBCCSG-01)," Japanese Journal of Clinical Oncology, Vo. 33, No. 8, pp. 371-376, Aug. 2003.
Scotlandi et al., "Effectiveness of Ecteinascidin-743 against Drug-sensitive and -resistant Bone Tumor Cells," Clinical Cancer Research, 8:3893-3903 (Dec. 2002).
Sessa et al., "Trabectedin for Women with Ovarian Carcinoma After Treatment with Platinum and Taxane Fails," Journal of Clinical Oncology, vol. 23,No. 9, pp. 1867-1874, Mar. 20, 2005.
Smyth, "Rationale for Drug Combinations," European Journal of Cancer, 39, 1816-1817 (2003).
Taamma et al., "Phase I Clinical Study of ecteinascidin-743 (ET-743)," Eur. J. Cancer, 33 Suppl. 8, S247-S248, 1997, Abstract.
Taamma, A. et al., "Ecteinascidin-743 (ET-743) 24 hours continuous infusion (CI): clinical and pharmacokinetic phase I study in solid tumor patients (PTS) Preliminary Results" 1998 ASCO Annual Meetings Proceedings, Abstract No. 890, 1998.
Taamma, A. et al., "Phase I clinical study of ecteinascidin-743 (ET-743) as a 24 hours continuous intravenous infusion (CI) in patients (PTS) with solid tumors (st): A progress report," ECCO, vol. 9, Abstract No. 1119, Sep. 18, 1997.

Tabor et al., "Anti oxidation Potential of Indole Compounds—Structure Activity Studies," Biological Reactive Intermediates IV, p. 833-836, 1990.
Takebayashi et al., "Poisoning of Human DNA Topoisomerase I by Ecteinascidin 743, An Anticancer Drug That Selectively Alkylates DNA in the Minor Groove." Proc. Natl. Acad. Sci. USA 96, 7196-201 1999.
Takahashi et al., "Ecteinascidin 743 (ET-743) and doxorubicin produce synergistic cytotoxic effects in soft tissue sarcoma lines HT-1080 and HS-18," Clinical Cancer Research, vol. 6, Abstract 208 (Nov. 2000).
Takahashi et al., "Sequence-dependent Enhancement of Cytotoxicity Produced by Ecteinascidin 743 (ET-743) with Doxorubicin or Paclitaxel in Soft Tissue Sarcoma Cells," Clinical Cancer Research, 7: 3251-3257 (Oct. 2001).
Takahashi et al., "Sequence-dependent Synergistic Cytotoxicity of Ecteinascidin-743 and Paclitaxel in Human Breast Cancer Cell Lines in Vitro and in Vivo," Cancer Research, 62: 6909-6915 (Dec. 1, 2002).
Twelves et al., "A Phase I and Pharmacokinetic (PK) study of ET-743 evaluating a 3 hours (h) intravenous (iv) infusion (I) in patients (pts) with solid tumors," Clinical Cancer Research, Abstract #307, 5 (11, suppl. 3790S-3791S) 1999.
Twelves, C.J. et al., "Phase I clinical and pharmacokinetic (PK) study of ecteinascidin-743 (ET-743) given as a one hour infusion every 21 days," 1998 ASCO Annual Meeting Proceedings, Abstract No. 889, 1998.
Twelves, C.J. et al., "Phase I and pharmacokinetic study of ecteinascidin-743 (ET-743) given as a one hour infusion every 21 days," ECCO, vol. 9, Abstract No. 1107, Sep. 18, 1997.
Valoti, "Ecteinascidin-743, a New Marine Natural Product with Potent Antitumor Activity on Human Ovarian Carcinoma Xenografts," Clin. Cancer Res., vol. 4, pp. 1977-1983, Aug. 1998.
Valoti, G., et al., "Ecteinascidin-743 (ET-743), a marine natural compound, shows antitumor activity against human ovarian carcinoma xenografts," Novel Therapeutics and Pharmacology, p. S39, Abstract pp. 179, 1998.
van Kesteren et al. "Yondelis® (trabectedin, ET-743): The Development of an Anticancer Agent of Marine Origin" Anti-Cancer Drugs, vol. 14, No. 7, pp. 487-502, Aug. 2003.
Villalona-Calero, M. et al., "A phase I and pharmacokinetic study of ET-743, a novel DNA minor groove binder of marine origin, administered as a 1-hour infusion daily × 5 days," Annals Oncology, Abstract 453, 1998.
Villalona-Calero, M. et al., "Final results of a Phase I and pharmacokinetic (PK) study of the marine minor groove binder ET-743 on a daily × 5 schedule," 1999 ASCO Annual Meeting Proceedings, Abstract No. 691, 1999.
Wiesenthal, "Is one 'sensitive' drug better than another?" downloaded from internet website <<http://weisenthal.org/feedback.html>>, Feb. 4, 2002.
Wright et al., "Antitumor Tetrahydroisoquinonline Alkaloids from the Colonial Ascidian *Ecteinascidia turbinata*", J. Org. Chem., vol. 55, pp. 4508-4512, 1990.
Zewail-Foote, et al., "Ecteinascidin 743: A Minor Groove Alkylator that Bends DNA Toward the Major Groove," J. Med. Chem. 42, 2493-7, Jul. 15, 1999.
Burstein et al., "Phase I study of Doxil and Vinorelbine in Metastatic Breast Cancer," Annals of Oncology, vol. 10, pp. 1113-1116, 1999, XP8086751.
Delaloge et al., "Ecteinascidin (ET-743) in heavily pretreated refractory sarcomas: Preliminary evidence of activity," Eur. J. Cancer, vol. 35, suppl. 4, p. S271, Abstract No. 1080, Sep. 15, 1999.
D'Incalci et al., "Mode of action of Ecteinascidin-743 (ET-743)," Proceedings of the 1999 AACR-NCI-EORTC International Conference, Clinical Cancer Research, vol. 5, Supplement, pp. 3872s-3873s, Abstract of Plenary Session 7, Nov. 16-19, 1999.
Dorr and Van Hoff, "Doxorubicin," Cancer Chemotherapy Handbook, 1994, pp. 395-416.
European Medicines Agency (EMEA), "Scientific Discussion" from the European Public Assessment Report for Yondelis®, Revision 1, published Mar. 31, 2008, downloaded from the internet on Apr. 2, 2008, from the website <<http://www.ernea.europa.eu/humandocs/Humans/EPAR/yondelis/yondelis.htm>>.

(56) References Cited

OTHER PUBLICATIONS

Friereich et al., "Quantitative Comparison of Toxicity of Anticancer Agents in Mouse, Rat, Hamster, Dog, Monkey, and Man," Cancer Chemotherapy Reports, 50:4, May 1966, pp. 219-245.
Fukuyama et al., "Stereocontrolled Total Synthesis of Saframycin B," J. Am. Chem. Soc., 104, 4957-4958, 1982.
Garcia-Carbonero et al., "Population pharmacokinetics of ecteinascidin 743 in patients with advanced soft tissue sarcoma," Clinical Cancer Research, vol. 6, Supplement, Abstract 211, p. 4508s, NCI-EORTC-AACR Symposium on New Drugs in Cancer Therapy, Nov. 7-10, 2000.
Giovanna et al., "Importance of DNA repair mechanisms for the sensitivity of tumor cells to ET-743," Proceedings of the 1999 AACR-NCI-EORTC International Conference, Clinical Cancer Research, vol. 5, Supplement, p. 3790s, Abstract 303, Nov. 16-19, 1999.
Gore et al., "Phase I Combination Study of Trabectedin and Capecitabine in Patients With Advanced Malignancies," Poster Presentation, 42nd ASCO Annual Meeting held on Jun. 2-6, 2006, Atlanta, Georgia.
Hoekman at al., "A phase I/II study of dose-escalated docetaxel given two weekly in combination with a fixed dose of G-CSF," European Journal of Cancer, vol. 37, p. S76, Abstract 270, Oct. 22, 2001.
Hornicek et al., "In vitro effect of the tetrahydroisoquinoline alkaloid Ecteinascidin-743 (ET-743) on chondrosarcoma (CHSA) cells," Proceedings of the 1999 AACR-NCI-EORTC International Conference, Clinical Cancer Research, vol. 5, Supplement, p. 3790s, Abstract 304, Nov. 16-19, 1999.
Jimeno et al., "Pharmacokinetics (PK)/Pharmacodynamic (PD) Relationships in Patients (PT) Treated With Ecteinascidin-743 (ET-743) Given As 24 Hours Continuous Infusion (CI)," Journal of Clinical Oncology, ASCO Annual Meeting Proceedings, Abstract No. 744, May 15-18, 1999.
Jin et al., "The antitumor agent Ecteinascidin 743 (ET743), inhibits transcriptional activation of the MDR1 Gene by multiple inducers," Proceedings of the 1999 AACR-NCI-EORTC International Conference, Clinical Cancer Research, vol. 5, Supplement, p. 3790s, Abstract 302, Nov. 16-19, 1999.
Lopez-Lazaro et al., "Exploratory evaluation of the potential predictors for dose-limiting toxicities (DLTs) in patients treated with Ecteinascidin-743 (ET-743) as a 24-h intravenous (iv) infusion every 3 weeks and its relationship to pharmacokinetics (PK)," Proceedings of the 1999 AACR-NCI-EORTC International Conference, Clinical Cancer Research, vol. 5, Supplement, p. 3791s, Abstract 308, Nov. 16-19, 1999.
Lyass et al., "Phase I Study of Doxil-Cisplatin Combination Chemotherapy in Patients with Advanced Malignancies," Clinical Cancer Research, vol. 7, pp. 3040-3046, Oct. 2001, XP8086753.
Rosing et al., "Pharmacokinetics (PK) of Ecteinascidin-743 (ET-743) in three different phase I trials," Proceedings of the American Association for Cancer Research, vol. 40, pp. 81, abstract No. 542, Mar. 1999.
Ryan, D.P. "Studies with Ecteinascidin-743 (ET-743) a Marine Alkaloid," Cancer Invest, vol. 18 (suppl 1), pp. 112, abstract No. 87, Jan. 2000, from the Chemotherapy Foundation Symposium XVII Innovative Cancer Therapy for Tomorrow, Nov. 3-6, 1999, NewYork, NY.
Scotto et al., "Ecteinascidin 743, a novel chemotherapeutic agent that targets transcriptional activation of a subset of genes, including MDR1," Clinical Cancer Research , vol. 6, Supplement, Abstract 210, p. 4508s, NCI-EORTC-AACR Symposium on New Drugs in Cancer Therapy, Nov. 7-10, 2000.
Shertzer et al., "Protection Against Carbon Tetrachloride Hepatoxicity by Pretreatment with indole-3-carbinol," Exptl. Molec. Pathol., vol. 46, pp. 180-189 (1987).
Shertzer et al., "Protection from N-Nitrosodimethylamine Mediated Liver Damage by Indole-3-carbinol," Exptl. Molec. Pathol., vol. 47, pp. 211-218 (1987).
Taamma et al., "Ecteinascidin-743 (ET-743) 24 hour continuous intravenous infusion (CI) phase I study in solid tumors (ST) patients (pts)." Proceedings of the American Association for Cancer Research , vol. 39, pp. 323, abstract No. 2207, Mar. 1998.
Taamma et al., "Ecteinascidin-743 (ET-743) in heavily pretreated refractory sarcomas: early results of the French experience," Proceedings of the 1999 AACR-NCI-EORTC International Conference, Clinical Cancer Research, vol. 5, Supplement, p. 3791s, Abstract 309, Nov. 16-19, 1999.
Takebayashi et al., "Multidrug Resistance Induced by DNA Minor Groove Alkylation of Ecteinascidin 743 (Et743)," Proceedings of the 1999 AACR-NCI-EORTC International Conference, Clinical Cancer Research, vol. 5, Supplement, p. 3851s, Abstract 602, Nov. 16-19, 1999.
Takebayashi et al., "Nucleotide excision repair-dependent cytotoxicity of Ecteinascidin 743," Clinical Cancer Research, vol. 6, Supplement, Abstract 207, p. 4508s, NCI-EORTC-AACR Symposium on New Drugs in Cancer Therapy, Nov. 7-10, 2000.
Ten Hagen et al., "Pegylated Liposomal Tumor Necrosis Factor-Alpha Results in Reduced Toxicity and Synergistic Antitumor Activity after Systemic Administration in Combination with Liposomal Doxorubicin (Doxil) in soft tissue Sarcoma-Bearing Rats," Int. J. Cancer, vol. 97, pp. 115-120, 2002.
Twelves et al., "Phase I Trials with ET-743, a marine derived (MD) anticancer agent," Eur. J. Cancer, vol. 35, suppl. 4, p. S283, Abstract No. 1135, Sep. 15, 1999.
Twelves et al., "Phase I and pharmacokinetic study of YondelisTM (Ecteinascidin-743; ET-743) administered as an infusion over 1 h or 3 h every 21 days in patients with solid tumours," European Journal of Cancer, vol. 39, p. 1842-1851, 2003; available online Aug. 14, 2003.
van Kesteren et al. "Clinical Pharmacology of the Novel Marine-derived Anticancer Agent Ecteinascidin 743 Administered as a 1- and 3-h Infusion in a Phase I Study," Anti-Cancer Drugs, vol. 13, No. 4, pp. 381-393, Apr. 2002.
Weiwei et al., "Potent antitumor activity of ET-743 against human soft tissue sarcoma cell lines," Proceedings of the 1999 AACR-NCI-EORTC International Conference, Clinical Cancer Research, vol. 5, Supplement, p. 3790s, Abstract 305, Nov. 16-19, 1999.
Zelek et al., "Preliminary results of phase II study of ecteinascidin (ET-743) with the 24 hour (H) continuous infusion (CI) q3week schedule in pretreated" Clinical Cancer Research, vol. 6, Supplement, Abstract 212, pp. 4508s-4509s, NCI-EORTC-AACR Symposium on New Drugs in Cancer Therapy, Nov. 7-10, 2000.
Aboussekhra, A. et al. "Mammalian DNA Nucleotide Excision Repair Reconstituted with Purified Protein Components" Cell 1995, 80, 859-868.
Bootsma, D. et al. The Genetic Basis of Human Cancer, 1$^{st}$ ed.; Vogelstein B, Kinzler KW Eds.; McGraw Hill: Toronto, 1998; pp. 245-274.
Bueren, J. A. et al. Generation of DNA double strand breaks Turing trabectedin DNA damage measured trough induction of γH2AX [abstract]. In: American Association for Cancer Research Annual Meeting: Proceedings; Apr. 14-18, 2007; Los Angeles, CA. Philadelphia (PA): AACR; 2007. Abstract nr 1965; and the corresponding poster presented in said congress.
Casali et al., "Activity of Ecteinascidin-743 (ET-trabectedin) 3-hour Infusion in Adult and Childhood Small Round Cell Sarcomas," ASCO Annual Meeting, 2003, Abstract 962.
Chinese J. New Drugs Clin. Rem., 2001, pp. 216, 219.
Cvetkovic et al., "ET-743," Drugs, vol. 62(8), pp. 1185-1192, 2002.
Damia, G. et al. ET743-Induced changes in gene expression in murine cells defective in nucleotide excision repair [abstract]. In: AACR-NCI-EORTC International Conference on Molecular Targets and Cancer Therapeutics; 2001 Oct. 22-Nov. 2; Miami, US. Philadelphia (PA): ACCR, 2001. Abstract No. 666.
Erba, E. et al. "Ecteinascidin-743 (ET-743), a natural marine compound, with a unique mechanism of action" Eur. J. Cancer 2001, 37, 97-105.
Garcia-Carbonero et al., "Ecteinascidin-743 (ET-743) for Chemotherapy-Naïve Patients with Advanced Soft Tissue Sarcomas: Multicenter Phase II and Pharmacokinetic Study," J. Clin. Oncol. 23:5484-5492, 2005.
Gogas et al., "Neoadjuvant Chemotherapy with a Combination of Pegylated Liposomal Doxorubicin (Caelyx®) and Paclitaxel in Locally Advanced Breast Cancer: A Phase II Study by the Hellenic Cooperative Oncology Group," Annals of Oncology, pp. 1737-1742, 2002.

(56) References Cited

OTHER PUBLICATIONS

Grazziotin Soares, D. et al. "Low cytotoxicity of ecteinascidin 743 in yeast lacking the major endonucleolytic enzymes of base and nucleotide excision repair pathways" Biochemical Pharmacology 2005, 70, 59-69.

Grazziotin Soares, D. et al. "Replicationn and homologous recombination repair regulate DNA double-strand break formation by the antitumor alkylator ecteinascidin 743" PNAS 2007, 104, 13062-13067.

Grosso, F. et al. Trabectedin (T) in soft tissue sarcomas (STS) carrying a chromosomal translocation: an exploratory analysis [abstract]. In: 13th CTOS Annual Meeting; Nov. 1-3, 2007; Seattle, WA. p. 51. Abstract nr 900; and the corresponding oral presentation presented en said congress.

Herrero, A. B. et al. "Cross-Talk between Nucleotide Excision and Homologous Recombination DNA Repair Pathways in the Mechanism of Action of Antitumor Trabectedin" Cancer Res. 2006, 66, 8155-8162.

Hosomi et al., "Phase I Study of Cisplatin and Docetaxel Plus Mitomycin C in Patients with Metastatic Non-Small Cell Lung Cancer," Jpn. J. Clin. Oncol., 29(11), pp. 546-549, 1999.

Ilson et al., "A Phase II Trial of Paclitaxel and Cisplatin in Patients with Advanced Carcinoma of the Esophagu," Cancer J, 6(5), 316-23, 2000.

Italiano, A. et al. ERCC5 (XPG) status and clinical activity of trabectedin in patients with advanced soft-tissue sarcoma [abstract]. In: Proceedings of the 101th Annual Meeting of the American Association for Cancer Research; Apr. 17-21, 2010; Washington, DC. Philadelphia (PA): AACR; 2010. Abstract nr 2699; and the corresponding poster presented in said congress.

Kesteren Ch. Van et al. "Yondelis® (trabectedin, ET-743): the development of an anticancer agent of marine origin" Anti-Cancer Drugs 2003, 14, 487-502.

Kononen, J. et al. "Tissue microarrays for high-throughput molecular profiling of tumor specimens" Nature Med. 1998, 4, 844-847.

Kraemer, K. H. et al. "The Role of Sunlight and DNA Repair in Melanoma and Nonmelanoma Skin Cancer. The Xeroderma Pigmentosum Paradigm" Arch. Dermatol. 1994, 130, 1018-1021.

Kraemer, K. H. et al. "Xeroderma Pigmentosum. Cutaneous, Ocular, and Neurologic Abnormalities in 830 Published Cases" Arch. Dermatol. 1987, 123, 241-250.

Krafft, A. E. et al. "Optimization of the Isolation and Amplification of RNA From Formalin-fixed, Paraffin-embedded Tissue: The Armed Forces Institute of Pathology Experience and Literature Review" Mol. Diagn. 1997, 2, 217-230.

Le Morvan, V. et al. Genetic polymorphisms of the XPG and XPD nucleotide excision repair genes in sarcoma patients [abstract]. In: Proceedings of the 96th Annual Meeting of the American Association for Cancer Research; Apr. 16-20, 2005; Anaheim/Orange County, CA. Philadelphia (PA): AACR; 2005. Abstract No. 4099.

Le Morvan, V. et al. "Genetic polymorphisms of the XPG and XPD nucleotide excision repair genes in sarcoma patients" Int. J. Cancer 2006, 119, 1732-1735.

Le Page, F. et al. "Transcription-Coupled Repair of 8-oxoGuanine: Requierement for XPG, TFIIH, and CSB and Implications for Cockayne Syndrome" Cell 2000, 101, 159-171.

Martinez, N. et al. "Transcriptional signature of Ecteinascidin 743 (Yondelis, Trabectedin) in human sarcoma cells explantes from chemo-naïve patients" Mol. Cancer Ther. 2005, 4, 814-823.

McMeekin et al., "Trabectedin (T) in Relapsed Advanced Ovarian Cancer (ROC): A Pooled Analysis of Three Phase II Studies," Journal of Clinical Oncology, 25(18S), Abstract No. 5579, 2007 ASCO Annual Meeting.

Moneo, V. et al. "Extreme Sensitivity to Yondelis® (Trabectedin, ET-743) in Low Passaged Sarcoma Cell Lines Correlates With Mutated p53" J. Cell. Biochem. 2007, 100, 339-348.

Monk et al., "A Randomized Phase III Study of Trabectedin With Pegylated Liposmal Doxorubicin (PLD) Versus PLD in Relapsed, Recurrent Ovarian Cancer (OC)," Annals of Oncology, 19(8), 2008.

Mu, D. et al. "Reaction Mechanism of Human DNA Repair Excision Nuclease" J. Biol. Chem. 1996, 271, 8285-8294.

Mudgett. J. S. et al. "Isolation of the Functional Human Excision Repair Gene ERCC5 by Intercosomid Recombination" Genomics 1990, 8, 623-633.

Nouspikel, T. et al. "Mutations that disable the DNA repair gene XPG in a xeroderma pigmentosum group G patient" Hum. Mol. Genet. 1994, 3, 963-967.

O'Brien et al., "Reduced Cardiotoxicity and Comparable Efficacy in a Phase III Trial of Pegylated Liposomal Doxorubicin HCl (Caelyx™/Doxil®) Versus Conventional Doxorubicin for First-Line Treatment of Metastatic Breast Cancer," Annals of Oncology, vol. 15, pp. 440-449, 2004.

O'Donovan, A. et al. "Identical defects in DNA repair in xeroderma pigmentosum group G and rodent ERCC group 5" Nature 1993, 363, 185-188.

Pasetto et al., "Improved Tolerability of Chemotherapy in Soft Tissue Sarcomas: Old and New Strategies," Expt. Rev. Antican. Ther., vol. 3(2), pp. 167-178, 2003.

Pourquier, P. et al. Nucleotide excision repair-mediated cytotoxicity of ecteinascidin 743, a novel anticancer agent in clinical trials [abstract]. In: Proceedings of the 92nd Annual Meeting of American Association for Cancer Research; Mar. 24-28, 2001; New Orleans, LA, USA. Philadelphia (PA): AACR; 2001. p. 556. Abstract No. 2987.

Rimassa et al., "Unexpected Low Efficacy of Stealth Liposomal Doxorubicin (Caelyx) and Vinorelbine in Metastatic Breast Cancer," Breast Cancer Research and Treatment, 77, 2003, pp. 185-188.

Rose et al., "A Phase I Trial of Prolonged Oral Etoposide and Liposomal Doxorubicin in Ovarian, Peritoneal, and Tubal Carcinoma: A Gynecologic Oncology Group Study," Gynecologic Oncology, 85, 2002, pp. 136-139.

Rosell, R. et al. Expression of XPG mRNA and protein as potential biomarker of response to trabectedin in sarcoma patients [abstract]. In: AACR-NCI-EORTC International Conference on Molecular Targets and Cancer Therapeutics; Oct. 22-26, 2007; San Francisco, CA. Philadelphia (PA): AACR, 2007. Abstract nr C127; and the corresponding poster presented in said congress.

Rosell, R. et al. DNA repair efficiency as a model for personalizaed therapy with Trabectedin [abstract]. In: AACR Molecular Diagnostic in Cancer Therapeutic Development; Sep. 17-20, 2007; Atlanta, GA. Philadelphia (PA): AACR; 2007. p. 44. Abstract nr A57; and the corresponding poster presented in said congress.

Schöffski, P. et al. DNA repair functionality as a molecular signature for sensitivity(S)/resistance(R) in sarcoma patients (pts) treated with trabectedin (ET-743, Yondelis®) [abstract]. In: American Association for Cancer Research Annual Meeting: Proceedings; Apr. 14-18, 2007; Los Angeles, CA. Philadelphia (PA): AACR; 2007. Abstract nr 144; and the corresponding poster presented in said congress.

Shimizu et al., "Phase I Study of Docetaxel and Cyclophosphamide in Patients with Advanced or Recurrent Breast Cancer," Breast Cancer, 10(2), pp. 140-148, Apr. 2003.

Sparano et al., "Phase I Trial of Pegylated Liposomal Doxorubicin and Docetaxel in Advanced Breast Cancer," J. Clinical Oncology, vol. 19(12), pp. 3117-3125, 2001.

Specht, K. et al. "Quantitative Gene Expression Analysis in Microdissected Archival Formalin-Fixed and Paraffin-Embedded Tumor Tissue" Am. J. Pathol. 2001, 158, 419-429.

Stevens, E. et al. Ecteinascidin-743 (ET-743) and Transcription-Coupled Nucleotide Excision Repair (TC-NER): Translational and Clinical Study in Ovarian Cancer [abstract]. In: Proceedings of the 94th Annual Meeting of the American Association for Cancer Research; 2003 Jul. 11-14, 2003; Washington, DC. Philadelphia (PA): AACR; 2003. Abstract No. 468.

Stevens, E. V. et al. "Predicting cisplatin and trabectedin drug sensitivity in ovarian and colon cancers" Mol. Cancer Ther. 2008, 7, 10-18.

Takebayashi, Y. et al. "Antiproliferative activity of ecteinascidin 743 is dependent upon transcription-coupled nucleotide-excision repair" Nature Med. 2001, 7, 961-966.

Takebayashi, Y. "Loss of heterozygosity of nucleotide excision repair factors in sporadic ovarian, colon and lung carcinomas: implications for their roles of carcinogenesis in human solid tumors" Cancer Lett. 2001, 174, 115-125.

(56) References Cited

OTHER PUBLICATIONS

Taron, M. et al. BRCA1 expression and customized chemotherapy [abstract]. In: Eurocancer. XX Congrès; Jun. 26-28, 2007; Paris. Paris: John Libbey Eurotext, 2007. pp. 107-108.
Tercero, J. C. et al. Predicting sarcoma patients response to trabectedin treatment with molecular markers detected by inmunohistochemistry [abstract]. In: AACR International Conference: Molecular Diagnostics in Cancer Therapeutic Development; Sep. 22-25, 2008; Philadelphia, PA. Philadelphia (PA): AACR, 2008. p. 44. Abstract nr B8; and the corresponding poster presented in said congress; and the corresponding poster presented in said congress.
van Steeg, H et al. "Xeroderma pigmentosum and the role of UV-induced DNA damage in skin cancer" *Mol. Med. Tod.* 1999, 5, 86.
Villalona-Calero et al., "A Phase I and Pharmacokinetic Study of Ecteinascidin-743 on a Daily × 5 Schedule in Patients with Solid Malignancies," Clinical Cancer Research, vol. 8, pp. 75-85, 2002.
Wakasugi, M. et al. "The Non-catalytic Function of XPG Protein during Dual Incision in Human Nucleotide Excision Repair" *J. Biol. Chem.* 1997, 272, 16030-16034.
Wirth et al., "Maillard Reaction of Lactose and Fluoxetine Hydrochloride, a Seconfary Amine," Journal of Pharmaceutical Sciences, 87(1), pp. 31-39, Jan. 1998.
Yondelis Summary of Product Characteristics as authorised by EMA in 2007.
Zeltia Group Annual Report 2002.
Zeltia, Junta General de Accionistas 2003.
Zewail-Foote, M. et al. "The inefficiency of incisions of ecteinascidin 743-DNA adducts by the UvrABC nuclease and the unique structural feature of the DNA adducts can be used to explain the repair-dependent toxicities of this antitumor agent" Chemistry & Biology 2001, 8, 1033-1049.
Andya at al., "Mechanisms of Aggregate Formation and Carbohydrate Excipient Stabilization of Lyophilized Humanized Monoclonal Antibdoy Formulations", 2003, 5(2), pp. 1-11, AAPS PharmSci.
Scotto, Anticancer Drugs, May 2002, 13 Suppl 1, S3-6.
U.S. Appl. No. 10/257,856, filed Mar. 31, 2003, Andres Francesch.
U.S. Appl. No. 12/094,744, filed Nov. 17, 2008, Kathleen Scotto.
U.S. Appl. No. 12/552,347, filed Sep. 2, 2009, Naoto Takahashi.
Carter et al., "Trabectedin, A Review of its Use in Soft Tissue Sarcoma and Ovarian Cancer," Drugs, 70(3), pp. 355-376, 2010.
Demetri et al., "Ecteinascidin (ET-743) Shows Promising Activity in Distinct Populations of Sarcoma Patients: Summary of U.S.-Based Phase II Trials," 2000, ASCO Online, retrieved from <<http:www.asco.org/prof/me/html/00abstracts/mel/pham_2177.htm>>, retrieved on Oct. 4, 2002.
Fung-Kee-Fung et al., "Optimal Chemotherapy Treatment for Women with Recurrent Ovarian Cancer," Current Oncology, 14(5):195-208, 2007.
Green et al., "Southwest Oncology Group Standard Response Criteria, Endpoint Definitions and Toxicity Criteria," Investigational New Drugs, 10:239-253, 1992.
Lu, Wan-Liang et al., "A pegylated liposomal platform: pharmacokinetics, pharmacodynamics, and toxicity in mice using doxorubicin as a model drug," J of Pharmacological Sciences, 95, 381-389, 2004.
Miller et al., "Reporting Results of Cancer Treatment," American Cancer Society, 47:207-214, 1981.
Rustin et al., "Use of CA-125 in Clinical Trial Evaluation of New Therapeutic Drugs for Ovarian Cancer," Clinical Cancer Research, 10:3919-3926, 2004.
Summons to Attend Oral Proceedings Pursuant to Rule 115(1) EPC for European Patent No. 1827500, Pharma Mar S.A., dated Oct. 6, 2011, 14 pages total.
Takahashi et al., "Ecteinascidin 743 (ET-743) and doxorubicin produce synergistic cytotoxic effects in soft tissue sarcoma lines HT-1080 and HS-18," Clinical Cancer Research, vol. 6, Abstract 209, Nov. 7-10, 2000.
Therasse et al., "New Guidelines to Evaluate the Response to Treatment in Solid Tumors," J. National Cancer Inst., 92(3):205-16, 2000.

Trosko et al., "Mechanism of up-regulated Gap Junctional Intercelluar Communication during Chemoprevention and Chemotherapy of Cancer," Mutation Research, 480-481, pp. 219-229, 2001.
Zeltia SA and Dependent Companies, Management Report, Annual Report, 1999.
Notices of Opposition filed against EP Patent No. 1365808 by Teva Pharmaceutical Industries Ltd., Nov. 24, 2011.
U.S. Appl. No. 12/091,540, filed Jun. 4, 2008, Pilar Calvo Salve.
U.S. Appl. No. 12/738,722, filed Apr. 19, 2010, Rafael Rosell Costa.
Blay, J., et al. "Phase I Combination Study of Trabectedin and Doxorubicin in Patients with Soft-Tissue Sarcoma," Clinical Cancer Research, 2008, 14(20); 6656-6662.
Chu, Q., et al, "Phase I and Pharmacokinetic Study of Sequential Paclitaxel and Trabectedin Every 2 Weeks in Patients with Advanced Solid Tumors," Clinical Cancer Research, 2008; 16 (9) , pp. 2656-2665.
Gore, L., et al., "Phase I combination study of trabectedin (T) and capecitabine (C) in patients with advanced malignancies," Journal of Clinical Oncology, 2006 ASCO Annual Meeting Proceedings, vol. 24, No, 18S (Jun. 20 Supplement), 2008: Abstract 2079.
Grasselli, G. et al., "Phase I and Pharmacokinetic (PK) study of Ecteinascidin-743 (ET, Trabectedin) and Cisplatin (P) combination in pre-treated patients (pts) with selected advanced solid tumors," Abstract 542 of 39th Annual Meeting of American Society of Clinical (ASCO), May 31-Jun. 3, 2003.
Messersmith, W.A. et al., "Phase I trial of weekly trabectedin (ET-743) and gemcitabine in patients with advanced solid tumor,"Cancer Chemother. Pharmacol., 2008, 63, pp. 181-188.
Salazar, R., et al., "Clinical and Pharmacokinetic Phase I Combination Study of Trabectedin (T) and Carboplatin (C) in patients with advanced solid tumors," Abstract 424P of 31st ESMO (European Society for Medical Oncology) Congress, Sep. 29-Oct. 3, 2006.
von Mehren, M., et al., "A phase I study of the safety and pharmacokinetics of trabectedin in combination with pegylated liposomal doxorubicin in patients with advanced malignancies," Annals of Oncology, 2008, 19, pp. 1802-1809.
Von Mehren, M,, et al., "Phase I study of trabectedin (T) in combination with docetaxel (D) in patients with advanced malignancies," Journal of Clinical Oncology, 2006 ASCO Annual Meeting Proceedings, vol. 24, No. 18S (Jun. 20 Supplement), 2006: Abstract 2068.
Alexopoulos, "Phase II study of pegylated liposomal doxorubicin (Caelyx(R)) and docetaxel as first-line treatment in metastatic breast cancer," Ann. Oncol., 2004, 15(6):891-5.
Chabner, "Cytotoxic agents in the era of molecular targets and genomics," The Oncologist, vol. 7, suppl. 3, pp. 34-41, 2002.
Committee on Risk Assessment Methodology, "Issues in Risk Assessment. Appendix A: Workshop Summary—Maximum Tolerated Dose: Implications for Risk Assessment," National Research Council, National Academy of Sciences, National Academies Press, Washington DC, pp. 79-89, 1993.
D'Incalci et al., "Unique Features of the Mode of Action of ET-743", The Oncologist, 7, p. 210-216, Jun. 2002.
Donald et al, "Comparison of four modulators of drug metabolism as protectants against the hepatotoxicity of the novel antitumor drug yondelis (ET-743) in the female rat and in hepatocytes in vitro," Cancer Chemother Pharmacol, Apr. 2004, vol. 53, pp. 305-312.
Forouzesh et al., Proc. Am. Soc. Clin. Oncol. ASCO meeting, Abstract 373, Jun. 3, 2001, Internet Archive Entry from the website <<http://web.archive.org/web/*/http://www.asco.org/>>, 32 pages.
Gourley C. et al., "Malignant mixed Mesodermal Tumours—Biology and Clinical Aspects," European Journal of Cancer, 2002, vol. 38, No. 11, pp. 1437-1446.
Halm et al., "A phase II study of pegylated liposomal doxorubicin for treatment of advanced hepatocellular carcinoma," Ann. Oncol., 2000, 11(1):113-114.
Horstmann et al., "Risks and Benefits of Phase I Oncology Trials, 1991 through 2002," New England Journal of Medicine, vol. 352, pp. 895-904; Mar. 3, 2005.
Hussein et al., "A Phase II Trial of Pegylated Liposomal Doxorubicin, Vincristine, and Reduced-Dose Dexamethasone Combination Therapy in Newly Diagnosed Multiple Myeloma Patients," Cancer, Nov. 15, 2002, vol. 95, No. 10, pp. 2160-2168.

(56) References Cited

OTHER PUBLICATIONS

Lau et al., "A Phase I and Pharmacokinetic Study of Ecteinascidin-743 (Yondelis) in Children with Refractory Solid Tumors." Clinical Cancer Research, vol. 11, pp. 672-677, Jan. 15, 2005.
PR Newswire, PR Newswire, Oct. 14, 2001, 4 pages.
Puchalski et al., "Pharmacokinetics of Ecteinascidin 743 Administered as a 24-h Continuous Intravenous Infusion to Adult Patients with Soft Tissue Sarcomas associations with Clinical Characteristics, Pathophysiological Variables and Toxicity," Cancer Chemotherapy and Pharmacology, 2002, vol. 50, No. 4, pp. 309-319.
Schwartsmann G. et al., "Marine Organisms as a Source of New Anticancer Agents," The Lancet Oncology, 2001, vol. 2, No. 4, pp. 221-225.
United States Pharmacopeia/National Formulary, "2010 USP/NF:The Official Compendia of Standards," United States Pharmacopeial Convention, 28$^{th}$ Edition, vol. 1, p. 1441-1446.

* cited by examiner

PHARMACEUTICAL FORMULATIONS OF ECTEINASCIDIN COMPOUNDS

RELATED APPLICATIONS

Priority is claimed under 35 U.S.C. §119(e) for U.S. Provisional Application Ser. No. 60/623,813, filed Oct. 29, 2004. The entire disclosure of the priority application is considered as being part of the disclosure and is incorporated herein by reference.

The present invention relates to formulations. More particularly it relates to compositions and formulations of ecteinascidins, such as ecteinascidin 743.

BACKGROUND OF THE INVENTION

Ecteinascidins have been identified, structurally characterized and synthetic methods for making them have been described. See for example, R. Sakai, et al., 1992, *Prco. Natl. Acad. Sci. USA* 89, pages 11456-11460, "Additional antitumor ecteinascidins from Caribbean tunicate: Crystal structures and activities in vivo"; R. Menchaca, et al., 2003, *J. Org. Chem.* 68(23), pages 8859-8866, "Synthesis of natural ecteinascidins (ET-729, ET-745, ET-759B, ET-736, ET-637, ET-594) from cyanosafracin B"; and I. Manzanares, et al., 2001, *Curr. Med. Chem.—Anti-Cancer Agents*, 1, pages 257-276, "Advances in the Chemistry and Pharmacology of Ecteinascidins, A Promising New Class of Anticancer Agents"; and references therein. These references describe ecteinascidins. Examples of ecteinascidins are provided by ET-743, ET-729, ET-745, ET-759A, ET-759B, ET-759C, ET-770, ET-815, ET-731, ET-745B, ET-722, ET-736, ET-738, ET-808, ET-752, ET-594, ET-552, ET-637, ET-652, ET-583, ET-597, ET-596, ET-639, ET-641, and derivatives thereof, such as acetylated forms, formylated forms, methylated forms, and oxide forms, such as N-oxide forms.

The structural characterizations of such ecteinascidins are not given again explicitly herein because from the detailed description provided in such references and citations therein; any person of ordinary skill in this technology is capable of obtaining such information directly from the sources cited here and related sources.

At least one of the ecteinascidin compounds, ET-743, has been extensively studied, and it will be referred to specifically herein to illustrate features of this invention.

Ecteinascidin 743 (ET-743) is a tetrahydroisoquinoline alkaloid isolated from the marine tunicate *Ecteinascidia turbinata* and has the following structure:

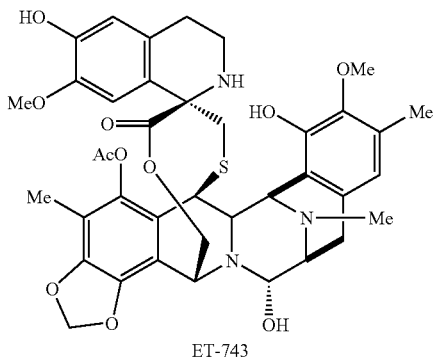

ET-743

A pharmaceutical composition comprising ET-743 in combination with a pharmaceutically acceptable carrier, diluent or excipient is claimed in U.S. Pat. No. 5,256,663.

A recent review of ET-743, its chemistry, mechanism of action and preclinical and clinical development can be found in van Kesteren, Ch. et al., 2003, *Anti-Cancer Drugs*, 14 (7), pages 487-502: "Yondelis (trabectedin, ET-743): the development of an anticancer agent of marine origin", and references therein.

ET-743 possesses potent antineoplastic activity against a variety of human tumour xenografts grown in athymic mice, including melanoma and ovarian and breast carcinoma.

In clinical phase I studies of ET-743, promising responses were observed in patients with sarcoma and breast and ovarian carcinoma. Therefore this new drug is currently under intense investigation in several phase II clinical trials in cancer patients with a variety of neoplastic diseases.

As it is explained in WO 0069441, incorporated in full by reference, ET-743 is supplied and stored as a sterile lyophilised product, having ET-743, mannitol and a phosphate buffer. A preferred formulation is one obtained from 0.9% sodium chloride or other suitable infusion vehicle, 250 µg of ET-743 with 250 mg of mannitol, 34 mg of monopotassium phosphate, and phosphoric acid to adjust the pH. This formulation is then reconstituted and diluted for intravenous injection.

ET-743 is a complex chemical entity, as revealed by its structural features. In addition, ET-743 exhibits limited aqueous solubility, and its stability, particularly in biocompatible forms and formulations, is difficult to predict and achieve. These characteristics challenge the ordinary skills and conventional methodologies in this technology, particularly when it comes to the preparation of ET-743 formulations that are to be readily used for medical purposes. Such uses preferably rely on formulations whose characteristics include one or more of the following: biocompatibility, stability under ambient conditions, or under conditions that are as near to ambient conditions as possible, with a shelf life that is as long as possible, and easy reconstitutability to form reconstituted solutions that are as stable under ambient, or near ambient conditions, for as long as possible.

However, conventional formulations and methodologies for preparing such formulations do not provide desirable features and characteristics such as those referred to above. For example, the cited review of 2003 by van Kesteren Ch. et al. reports that ET 743 has limited aqueous solubility. However, by adjustment of the pH to 4, adequate concentrations of ET 743 could be reached. Instability of ET 743 in aqueous solution necessitated lyophilization in order to increase the storage stability of the pharmaceutical product. ET-743 is currently formulated as a sterile lyophilized product containing 250 pg active substance per dosage unit, 250 mg mannitol as a bulking agent and 0.05 M phosphate buffer at pH 4 in order to solubilize ET-743. This formulation is unstable with long-term storage at refrigerated and room temperature, and should therefore be stored between −15 and −25° C., protected from light. Reconstitution is performed by adding 5 ml Water for Injection, with subsequent dilution in normal saline before i.v. infusion. The reconstituted solution is stable at ambient temperature for up to 24 h.

In practice this product containing 250 µg of ET-743 is manufactured by freeze-drying 5 ml of solution containing ET-743, mannitol, phosphate buffer and water in a moulded vial. Moulded vials containing 1 mg ET-743 are also manufactured by freeze-drying 20 ml of the solution.

Freeze-drying typically involves freezing the solution, reducing the pressure for a period of primary drying to remove water vapour from the frozen material by sublimation and give a semi-dried mass, and increasing the temperature for a period of secondary drying to remove residual water from the semi-dried mass. The vials are then sealed.

The above-described conventional ET-743 formulation suffers from several disadvantages. One of them is that the lyophilised ET-743 formulation has to be stored at about −20° C. to prevent decomposition of the ET-743 in order to achieve a shelf life of at least 18 months.

In addition, ET-743 formulations face the problem of formation of relatively large amounts of ET-701 as impurity. ET-701 is the main impurity produced during the lyophilisation process and during storage of the ET-743 formulation. It comes from the hydrolysis of ET-743 and has the following structure:

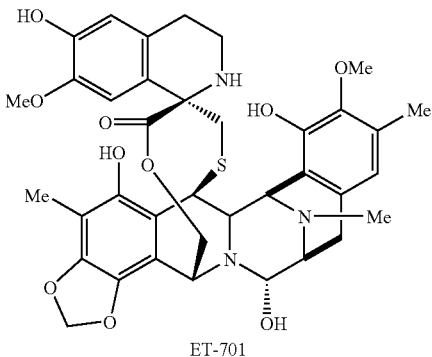

ET-701

Formation of impurities, however, diminishes or even forestalls the ability to standardize formulations. It is consequently desirable to provide formulations and methods for making the same that provide embodiments whose composition does not readily and unpredictably change by the uncontrolled formation of impurities.

Furthermore, another disadvantage of the above-described conventional ET-743 formulation methodology is that in order to obtain the lyophilised formulation it is necessary to freeze-dry a relatively large amount of solution with fill volumes in the order of 5 to 20 ml. In contrast, it would be desirable to develop a manufacturing methodology for formulations with compounds as complex as ET-743 that permits the making of formulations with higher active substance concentrations, so that the volumes to be handled are consequently reduced. Time and energy are needed in conventional methods for the step of freeze-drying, in view of the relatively high fill volumes of 5 or 20 ml. Along with the time and energy, there is also the risk of decomposition of the ET-743, particularly in the secondary drying.

In view of the potential of ET-743 formulations as antitumoral agents, there is a need to provide a formulation that can solve problems that conventional formulations and manufacturing methodologies do not address or do not completely solve. These problems include the problem of stability of ET-743. Embodiments of ET-743 formulations should preferably exhibit favourable freeze-drying properties, should preferably be susceptible of ready reconstitution, and they should preferably exhibit dilution properties, such as upon dilution with infusion fluid, while presenting as many as the desirable characteristics of formulations for medical use as referred to herein. As indicated above, embodiments of ET-743 formulations should be stable during long term storage. In addition, the formulation and its manufacturing methodology should satisfy biocompatibility standards and should thus allow for the effective use of a formulation vehicle that is non-toxic, at least at the concentrations used for infusion.

A general review of excipient-drug interactions in parental formulations is provided by Akers, M J, in Journal of Pharmaceutical Sciences, 91, 2002, 2283-2300. This reference provides, inter alia, a section on bulking agents and lyoprotectants, including this subject matter in the context of lyophilisation.

It is envisaged that the methodologies and formulations developed in the context of this invention are applicable to other ecteinascidins, in addition to ET-743.

OBJECTS OF THE INVENTION

It is an object of this invention to provide stable formulations of ecteinascidins, and methods of making such formulations.

It is a specific object of this invention to provide a new stable formulation of ET-743. In particular, a formulation is needed which has greater storage stability. There is especially a need to avoid the formation of impurities. In particular, it is desirable to provide embodiments of formulations that are substantially free of ET-701.

Furthermore, other objects of this invention concern the development of manufacturing methodologies that permit the preparation of ET-743 formulations with ET-743 concentrations that are higher than those achieved by conventional means. Additional objects concern the development of processes for improving the solubility of chemical entities as complex as ET-743, eventually increasing the ET-743 concentration in the solution for lyophilising, and thus reducing the fill volume in the vials before lyophilising the formulation.

SUMMARY OF THE INVENTION

According to the present invention there is provided ET-743 compositions which comprise ET-743 and a disaccharide, and methods for preparing such compositions. Preferred embodiments of such compositions are of pharmaceutical purity.

Other embodiments of this invention are provided by compositions that comprise an ecteinascidin and a disaccharide.

Some embodiments of such compositions are provided by lyophilised formulations which comprise an ecteinascidin such as ET 743 and a disaccharide. Methods for preparing such formulations are provided.

The invention provides methods of reducing, or even substantially eliminating, the formation of impurities in ET-743 formulations. Some embodiments include methodology for reducing, or even substantially eliminating, ET-701 formation in ET-743 formulations.

The invention also provides methodology for more effectively handling formulations of an ecteinascidin such as ET-743, including methods for making higher concentration formulations and methods for reducing the fill volume of a vial when producing a lyophilised formulation.

The present invention also provides methods of solubilising complex chemical entities, such as ecteinascidins, including but not limited to ET-743. Such methods allow for the manufacturing of a more concentrated solution of ET-743 in bulk solution for lyophilising, leading to reduced fill volumes.

DETAILS OF THE INVENTION

We have found in the context of this invention that disaccharides stabilize ecteinascidin formulations. Ecteinascidins, including ET-743, are complex chemical entities whose behaviour in formulations is not predictable in terms of the behaviour of other unrelated chemical substances. Such behaviour is even more difficult to predict when at least one ecteinascidin is included as the active substance in a formulation that is to satisfy biocompatibility standards, including medical standards. We have further found in this regard that the use of disaccharides as bulking agents can drastically reduce the formation of impurities during the lyophilisation process and storage of ET-743 compositions.

When embodiments of this invention are to provide ET-743 formulations that are substantially free of other ecteinascidins such as ET-701, or at least with a content of ET-701 as low as possible, then ET-701 is regarded as an impurity whose presence in the formulation is to be at least reduced.

In addition, the use of disaccharides also improves the storage conditions allowing long term storage of the lyophilised formulation in a wide temperature range, including refrigeration conditions and room temperature. The term "stable" as used herein in, for example the expression "a stable ET-743 formulation", refers to a formulation that satisfies stability characteristics as reported herein and equivalents thereof, that are not possessed by conventional formulations and that are not achieved when the formulation is prepared by conventional manufacturing methodologies.

Examples of embodiments of the present invention are provided by novel pharmaceutically acceptable compositions comprising an ecteinascidin such as ET-743 and a disaccharide.

As noted in the introduction, ecteinascidins have been widely described. They may have the following general formula (I):

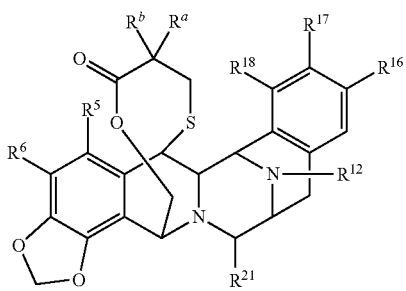

wherein:
$R^5$ is OH, alkoxy or alkanoyloxy;
$R^6$ is hydrogen, alkyl, alkenyl, alkynyl or aryl;
$R^{12}$ is hydrogen, alkyl, alkenyl, alkynyl or aryl;
$R^{16}$ is hydrogen, alkyl, alkenyl, alkynyl or aryl;
$R^{17}$ is OH, alkoxy or alkanoyloxy;
$R^{18}$ is OH, alkoxy or alkanoyloxy;
$R^{21}$ is H, OH, CN or another nucleophilic group; and
$R^a$ is hydrogen and $R^b$ is optionally substituted amino, or
$R^a$ with $R^b$ form a carbonyl function =O, or
$R^a$, $R^b$ and the carbon to which they are attached form a tetrahydroisoquinoline group.

In these compounds the substituents can be selected in accordance with the following guidance:

Alkyl and alkoxy groups preferably have from 1 to 12 carbon atoms. One more preferred class of alkyl and alkoxy groups has from 1 to about 6 carbon atoms, and most preferably 1, 2, 3 or 4 carbon atoms. Methyl, ethyl and propyl including isopropyl are particularly preferred alkyl groups in the compounds of the present invention. Methoxy, ethoxy and propoxy including isopropoxy are particularly preferred alkyl groups in the compounds of the present invention. Another more preferred class of alkyl and alkoxy groups has from 4 to about 12 carbon atoms, yet more preferably from 5 to about 8 carbon atoms, and most preferably 5, 6, 7 or 8 carbon atoms. As used herein, the term alkyl, unless otherwise modified, refers to both cyclic and noncyclic groups, although cyclic groups will comprise at least three carbon ring members.

Preferred alkenyl and alkynyl groups in the compounds of the present invention have one or more unsaturated linkages and from 2 to about 12 carbon atoms. One more preferred class of alkenyl or alkynyl groups has from 2 to about 6 carbon atoms, and most preferably 2, 3 or 4 carbon atoms. Another more preferred class of alkenyl or alkynyl groups has from 4 to about 12 carbon atoms, yet more preferably from 5 to about 8 carbon atoms, and most preferably 5, 6, 7 or 8 carbon atoms. The terms alkenyl and alkynyl as used herein refer to both cyclic and noncyclic groups.

Suitable aryl groups in the compounds of the present invention include single and multiple ring compounds, including multiple ring compounds that contain separate and/or fused aryl groups. Typical aryl groups contain from 1 to 3 separated or fused rings and from 6 to about 18 carbon ring atoms. Specially preferred aryl groups include substituted or unsubstituted phenyl, naphthyl, biphenyl, phenanthryl and anthracyl.

Suitable alkanoyloxy and alkanoyl groups have from 2 to about 20 carbon atoms, more preferably from 2 to about 8 carbon atoms, still more preferably from 2 to about 6 carbon atoms, even more preferably 2 carbon atoms. Another preferred class of alkanoyloxy groups has from 12 to about 20 carbon, yet more preferably from 14 to about 18 carbon atoms, and most preferably 15, 16, 17 or 18 carbon atoms.

The groups above mentioned may be substituted at one or more available positions by one or more suitable groups such as OR', =O, SR', SOR', SO$_2$R', NO$_2$, NHR', N(R')$_2$, =N—R', NHCOR', N(COR')$_2$, NHSO$_2$R', CN, halogen, C(=O)R', CO$_2$R', OC(=O)R' wherein each of the R' groups is independently selected from the group consisting of H, OH, NO$_2$, NH$_2$, SH, CN, halogen, =O, C(=O)H, C(=O)CH$_3$, CO$_2$H, substituted or unsubstituted C$_1$-C$_{12}$ alkyl, substituted or unsubstituted C$_2$-C$_{12}$ alkenyl, substituted or unsubstituted C$_2$-C$_{12}$ alkynyl and substituted or unsubstituted aryl. Suitable halogen substituents in the compounds of the present invention include F, Cl, Br and I.

Preferred compounds of the invention are those of general formula (I) wherein one or more of the following definitions will apply:
$R^5$ is an alkanoyloxy;
$R^6$ is methyl;
$R^{12}$ is methyl;
$R^{16}$ is methyl;
$R^{17}$ is methoxy;
$R^{18}$ is OH;
$R^{21}$ is H, OH or CN; and
$R^a$ is hydrogen and $R^b$ is an amido group, or
$R^a$ with $R^b$ form =O, or
$R^a$, $R^b$ and the carbon to which they are attached form a group of formula (II):

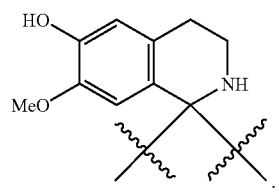 [SMILES: *C1(*)NCCc2cc(O)c(OC)cc21 ; "."]

Examples of compounds for the present invention include natural ecteinascidins, such as ecteinascidin 743 and other 1,4 bridged fused ecteinascidin compounds disclosed for example in U.S. Pat. Nos. 5,089,273, 5,478,932, 5,654,426, 5,721,362, 6,124,293, 5,149,804, Ser. No. 09/546,877, U.S. Pat. No. 5,985,876 and WO 01/77115.

Compounds of the following formula (III) are particularly preferred:

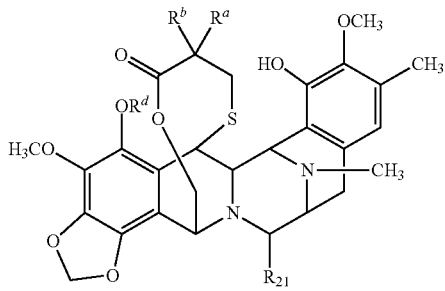

where $R^a$ is hydrogen and $R^b$ is amido of formula —NHR$^f$— where R$^f$ is alkanoyl, or $R^a$ with $R^b$ form =O, or $R^a$, $R^b$ and the carbon to which they are attached form a group of formula (II):

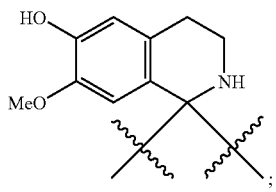

$R^d$ is alkanoyl; and $R^{21}$ is H, OH or CN.

The alkanoyl groups can be acetyl or higher, for example up to $C_{20}$.

Thus, preferred compounds of this invention include:

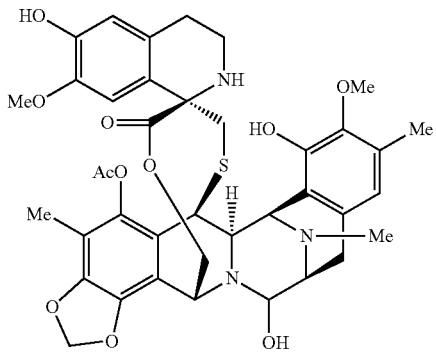
ET743

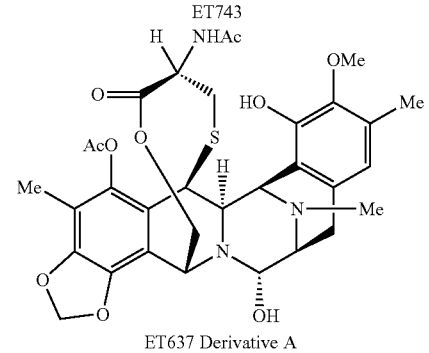
ET637 Derivative A

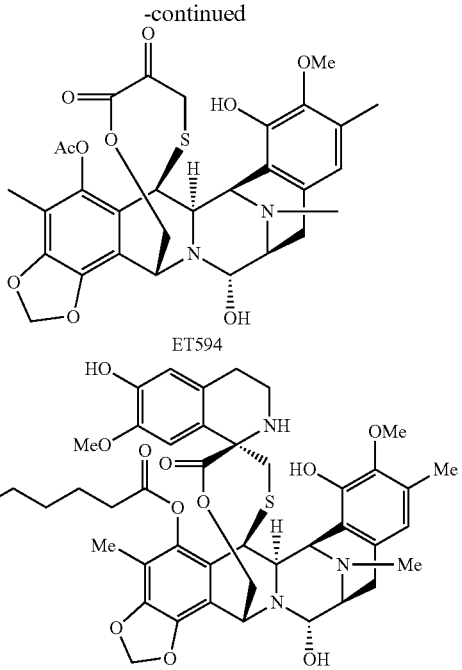
ET594

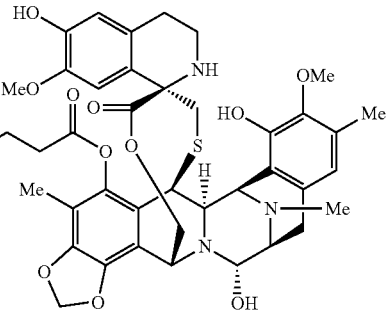
ET743 Derivative A

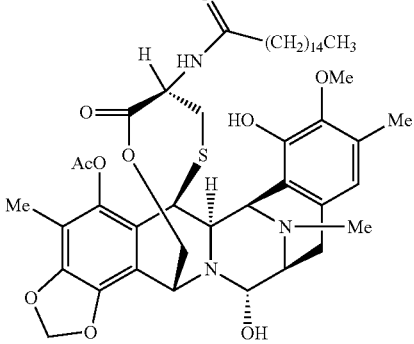
ET637 Derivative B or

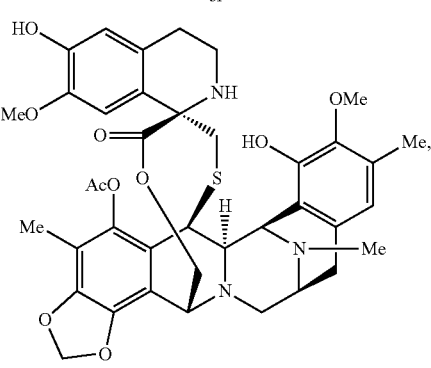
ET745 and related compounds with different acyl groups.

Ecteinascidin 743, also known as ET743 or ecteinascidin 743 is particularly preferred.

Examples of suitable disaccharides for the compositions of this invention include lactose, trehalose, sucrose, and combinations thereof. Additional examples of disaccharides that can be used in some embodiments of this invention include at least one of maltose, isomaltose, cellobiose, isosaccharose, isotrehalose, sorbose, turanose, melibiose, gentiobiose, and mixtures thereof. Sucrose is currently preferred.

In other embodiments of the invention, the composition comprises an ecteinascidin such as ET-743 and a lactose-free disaccharide. In other embodiments of the invention, the composition comprises an ecteinascidin such as ET-743 and a trehalose-free disaccharide. In other embodiments of the invention, the composition comprises an ecteinascidin such as ET-743 and a sucrose-free disaccharide. In other embodiments of the invention, the composition comprises an ecteinascidin such as ET-743 and a maltose-free disaccharide. In other embodiments of the invention, the composition comprises an ecteinascidin such as ET-743 and an isomaltose-free disaccharide. In other embodiments of the invention, the composition comprises an ecteinascidin such as ET-743 and a cellobiose-free disaccharide. In other embodiments of the invention, the composition comprises an ecteinascidin such as ET-743 and an isosaccharose-free disaccharide. In other embodiments of the invention, the composition comprises an ecteinascidin such as ET-743 and an isotrehalose-free disaccharide. In other embodiments of the invention, the composition comprises an ecteinascidin such as ET-743 and a sorbose-free disaccharide. In other embodiments of the invention, the composition comprises an ecteinascidin such as ET-743 and a turanose-free disaccharide. In other embodiments of the invention, the composition comprises an ecteinascidin such as ET-743 and a melibiose-free disaccharide. In other embodiments of the invention, the composition comprises an ecteinascidin such as ET-743 and a gentiobiose-free disaccharide.

Thus, in some embodiments, the composition of this invention contains less than 2% or less than 1% or less than 0.5% or less than 0.2% or less than 0.1% by weight of at least one of, preferably each of, lactose, trehalose, sucrose, maltose, isomaltose, cellobiose, isosaccharose, isotrehalose, sorbose, turanose, melibiose, and gentiobiose.

The terms "mixtures thereof" and "combinations thereof" as used herein refer to at least two entities that provide the antecedent basis for the terms "mixtures thereof" or "combinations thereof". By way of illustration, but not as a limitation, the terms "product comprising at least one of A, B, C, and mixtures thereof" refer to embodiments of the product for which any one of the following is satisfied: A is in the product; B is in the product; C is in the product; A and B are in the product; A and C are in the product; B and C are in the product; and A, B and C are in the product.

Furthermore, it is understood that terms such as "reacting", "forming", and related terms, applied to a chemical entity herein refer to any one of: (a) the chemical entity as such, and (b) the chemical entity in the form in which such entity is present in the reaction medium. Analogously, to name a chemical entity or to give its formula in the context of an operation or reaction step, or to name it or give its formula as being in a medium, whether solid or liquid, including products, formulations, and combinations, refers herein to any one of: (a) the entity as such, and (b) the entity in the form in which such entity is present in the medium. For example, naming an acidic chemical entity herein refers to whichever form or forms such entity is present in the context in which it is named. By way of illustration, but not as a limitation, naming the chemical entity "sodium chloride" or providing its chemical formula refers herein to the entity NaCl as such diatomic molecule, if such is the form in which sodium chloride is present in the relevant medium; it also refers to the collection of undissociated and/or dissociated chemical species if sodium chloride in the relevant medium is entirely or partially dissociated, including species in such medium that are solvated, part of cages, associated with other species, etc.

Any compound referred to herein is intended to represent such specific compound as well as certain variations or forms. In particular, compounds referred to herein may have asymmetric centers and therefore exist in different enantiomeric forms. All optical isomers and stereoisomers of the compounds referred to herein, and mixtures thereof, are considered within the scope of the formulations and methodologies of this invention. Thus any given compound referred to herein is intended to represent any one of a racemate, one or more enantiomeric forms, one or more diastereomeric forms, one or more atropisomeric forms, and mixtures thereof.

Furthermore, compounds referred to herein may exist as geometric isomers (i.e., cis and trans isomers), as tautomers, or as atropisomers. Additionally, any compound referred to herein is intended to represent hydrates, solvates, and polymorphs, and mixtures thereof when such forms exist in the medium. In addition, compounds referred to herein may exist in isotopically-labelled forms. All geometric isomers, tautomers, atropisomers, hydrates, solvates, polymorphs, and isotopically labelled forms of the compounds referred to herein, and mixtures thereof, are considered within the scope of the formulations and methodologies of this invention.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

The active substance or substances in the context of this invention can be of natural, semisynthetic or synthetic origin, including combinations of origins. In embodiments where, the active substance is an ecteinascidin such as ET-743, the ET-743 can be of natural origin, isolated for example from a tunicate of the genus *Ecteinascidia*, preferably the species *Ecteinascidia turbinata*. The ET-743 can be of synthetic or semisynthetic origin. Reference is made for example to WO 0069862 and WO 0187895, both of which are incorporated in full by reference.

The ratio of the active substance to the bulking agent in embodiments of this invention is determined according to the solubility of the bulking agent and, when the formulation is freeze dried, also according to the freeze-dryability of the bulking agent. It is envisaged that this ratio (w/w) can be about 1:1 in some embodiments, about 1:5 in other embodiments, about 1:10 in still other embodiments, while other embodiments illustrate ratios in the range from about 1:10 to about 1:1. It is envisaged that other embodiments have such ratios in the range from about 1:10 to about 1:100, and still further embodiments have such ratios in the range from about 1:100 to about 1:1500. When the active compound is ET-743, the ratio (w/w) of ET-743 to bulking agent is typically from about 1:100 to about 1:1500, preferably from about 1:200 to about 1:800, more preferably from about 1:250 to about 1:600, and even more preferably about 1:400.

The lyophilised material is usually presented in a vial which contains a specified amount of ecteinascidin or active compound. When the active compound is ET-743, active amounts are illustrated by 250 µg and 1 mg.

The present invention is not limited by specific container forms or designs, as long as the container is acceptable for its intended use and standards therefore. Embodiments of this invention are provided with a formulation contained in vials, preferably tubing vials.

The lyophilised formulations of this invention can be reconstituted and diluted to give a composition of this invention in the form of a solution ready for intravenous injection. The actual amounts of reconstituting fluid are not limiting features of embodiments of this invention. By way of illustrations, but not as limitations, embodiments of lyophilised formulations according to this invention are reconstituted with a volume of water. Most of such volumes do not exceed about 20 ml, with preferred volumes being in the range from about 1 ml to about 15 ml, more preferably in the range from about 1 ml to about 10 ml, and even more preferably in the range from about 1 ml to about 4 ml. When the active substance is embodied by ET-743, the reconstituted solution in such embodiments contains a concentration of ET-743 up to 500 Hg/ml, with concentrations of about 50 μg/ml, about 100 μg/ml, and about 250 μg/ml being preferred.

Reconstituted embodiments of the present invention can further be diluted if so desired, with this further dilution not being a limitation of the present invention. This further dilution is preferably carried out with an aqueous system which is usually 0.9% sodium chloride or 5% glucose. The reconstituted solution will be diluted depending on the concentration in the reconstituted solution and the desired concentration in the diluted solution.

Embodiments of ET-743 formulations according to this invention can be used in the treatment of a variety of cancers, including the treatment of any one of sarcoma, leiomyosarcoma, liposarcoma, osteosarcoma, ovarian cancer, breast cancer, melanoma, colorectal cancer, mesothelioma, renal cancer, endometrial cancer and lung cancer, and conditions with a plurality of such forms of cancer. It is understood that "treatment" in this context refers to an action that leads to an amelioration of the cancer condition(s). Embodiments of ET-743 formulations according to this invention can also be used in the treatment of refractory cancer conditions that have not responded favourably to other treatments. Furthermore, embodiments of formulations according to this invention can be used in the trials with laboratory tissues, including but not limited to clinical trials, analytical trials, and modelling assays.

Embodiments of this invention that comprise an ecteinascidin such as ET-743 are preferably administered by infusion. The infusing step is typically repeated on a cyclic basis, which may be repeated as appropriate over for instance 1 to 20 cycles. The cycle includes a phase of infusing ET-743 formulation, and usually also a phase of not infusing ET-743. Typically the cycle is worked out in weeks, and thus the cycle normally comprises one or more weeks of an ET-743 infusion phase, and one or more weeks to complete the cycle. A cycle of 3 weeks is preferred, but alternatively it can be from 1 to 6 weeks. The infusion phase can itself be a single administration in each cycle of say 1 to 72 hours, more usually of about 1, 3 or 24 hours; or an infusion on a daily basis in the infusion phase of the cycle for preferably 1 to 5 hours, especially 1 or 3 hours; or an infusion on a weekly basis in the infusion phase of the cycle for preferably 1 to 3 hours, especially 2 or 3 hours. A single administration at the start of each cycle is preferred. Preferably the infusion time is about 1, 3 or 24 hours.

The reconstituted and diluted solutions exemplify embodiments of this invention. A formulation that is reconstituted and diluted can be administered intra-venously using the available protocols. The dose will be selected according to the dosing schedule, having regard to the existing data on Dose Limiting Toxicity, on which see for example WO 0069441, WO 0236135 and WO 0339571, and van Kesteren, Ch. et al., 2003, Anti-Cancer Drugs, 14 (7), 487-502. These three WO patent specifications and this van Kesteren article are incorporated by specific reference.

Preferred dosing protocols include:
a) about 1.5 mg/m$^2$ body surface area, administered as an intravenous infusion over 24 hours with a three week interval between cycles;
b) about 1.3 mg/m$^2$ body surface area, administered as an intravenous infusion over 3 hours with a three week interval between cycles;
c) about 0.580 mg/m$^2$ body surface area, administered weekly as an intravenous infusion over 3 hours during 3 weeks and one week rest.

An ecteinascidin such as ET-743 can be used in combination with another drug. For example, it can be administered with another anti-tumour drug. The reader is referred to the list in WO 0069441 and WO 0236135, both of which are incorporated herein by specific reference. Examples of such other drugs include doxorubicin, cisplatin, paclitaxel, carboplatin, pegylated liposomal doxorubicin, docetaxel, capecitabine, and gemcitabine. Drugs with other modes of action can be used, including dexamethasone. Administration of the other drug can be before, during or after administration of the ecteinascidin such as ET-743.

Embodiments of formulations of this invention that contain an ecteinascidin such as ET-743 can be made by freeze-drying a composition of this invention in the form of a bulk solution including the ecteinascidin and disaccharide. Usually the bulk solution will be buffered, for example to a pH of about 4. Suitable buffering agents include phosphate buffer and citrate buffer. Other possible buffers can be used, such as phosphate/citrate buffer (a mixture of phosphate buffer and citrate buffer), lactate buffer, ascorbate buffer, tartaric/citrate buffer, bicarbonate/hydrochloric acid buffer, acetate buffer, succinate buffer and glycine/hydrochloric acid buffer. Mixtures of buffers can be used. Biocompatible buffers that permit the control of pH at a desired value provide additional embodiments of this invention.

Other components can be included in the bulk solution, for example surface-active agents such as polyoxyethylene 20 sorbitan monooleate or polyoxyl 40 stearate. Other possible surface-active agents include phospholipids, such as a lecithin; polyoxyethylene-polyoxypropylene copolymers, such as a Pluronic surfactant; polyoxyethylene esters of 12-hydroxysteraric acid, such as a Solutol surfactant; ethoxylates of cholesterol, such as diacyl glycerol, dialkyl glycerol; bile salts, such as sodium cholate, sodium deoxycholate; sucrose esters, such as sucrose monolaurate, sucrose monooleate; polyvinyl pyrrolidone (PVP); or polyvinyl alcohol (PVA).

The formulation is normally supplied as a vial containing the lyophilised product. This supply form, however, is not a limitation of the present invention. To provide a vial containing the lyophilised product, the bulk solution is added to a vial and freeze-dried. As mentioned herein, another object of the present invention is to provide a process for improving the solubility of an ecteinascidin such as ET-743 in order to increase the ecteinascidin concentration in the solution and reduce the fill volume in the vials before proceeding with the lyophilisation process. This methodology developed in the context of the present invention allows for the manufacturing of embodiments of bulk solution with active substance concentration that is higher than that obtained according to conventional methodologies. Reduced fill volumes in comparison with the conventional formulation with mannitol are therefore obtained with the present methodology. This reduction of fill volumes allows savings in time and energy during the freeze-drying step. In addition, there is also a decrease in the risk of decomposition of ET-743, particularly in the secondary drying.

As noted hereinabove, ET 743 has limited aqueous solubility, see for example van Kesteren, Ch., et al., 2003, *Anti-Cancer Drugs*, 14 (7), pages 487-502. Conventional methodologies provide for the adjustment of the medium pH to 4 with buffer, to solubilise ET 743. This pH control is conventionally achieved with a 0.05 M phosphate buffer at pH 4. It was found in the context of this invention that ET-743 solubility is improved in the bulk solution by forming a pre-solution of the ET-743 in an acid. With this pre-dissolution the ET-743 concentration in the bulk solution and the vial can be increased and the fill volume in the vials can be reduced. In these embodiments of the present invention, the fill volume is usually reduced by about 80% with respect to that of the conventional fill volume. By way of illustration, but not as limitations, embodiments of this invention provide a fill volume of 1 ml for a vial containing 0.25 mg ET-743, and 4 ml for a vial containing 1 mg ET-743. The fill volume can optionally reduced further in other embodiments of this invention by increasing the ET-743 concentration.

Conventional methodology comprised the dissolution of ET-743, mannitol and 0.05 M phosphate buffer at pH 4 together with water for injection; the solubility of the bulk solution was limited due to the low solubility of ET-743 in this medium. It was found in the context of the present invention that pre-treatment of ET-743 in an acid solution improves the ET-743 solubility and allows to have bulking solutions with higher concentrations of ET-743. Thus, the present invention provides processes useful for improving the solubility of ET-743 in the bulking solution that comprise dissolving ET-743 in an acidic medium, mixing the medium with ET-743 with other components of the bulking solution, and, optionally, adjusting the pH. In some illustrative, but not limiting, embodiments of this invention, pH adjustment is accomplished with a phosphate buffer. The acidic medium suitably contains no or substantially no buffering components, and usually consists of aqueous acid.

Illustrative embodiments of bulk solution for freeze drying according to the present invention are provided by a solution of ET-743 buffered at pH 4 with potassium dihydrogen phosphate and phosphoric acid with sucrose as bulking agent.

An illustrative embodiment of the methodology according to this invention provides as follows: ET-743 is dissolved in 0.1N phosphoric acid. Then water for injection ("WFI"), potassium dihydrogen phosphate, sucrose and ET-743 (pre-dissolved in 0.1N phosphoric acid) are mixed. Dissolution is visually checked before continuing, and dissolution is considered complete when it is so appreciated visually The pH of the solution is checked and adjusted to a value in the range from about 1 to about 5, more preferably in the range from about 2 to about 4.5, even more preferably in the rane from about 3 to about 4.5, and most preferably to a pH of about 4.0 by slow addition of a suitable acid. A preferred embodiment of such acid is phosphoric acid, in which case a preferred concentration is about 0.1N. A suitable base is optionally added for pH control. A preferred embodiment of such base is potassium hydroxide, preferably in solution, in which case a preferred concentration is about 0.1N. The volume is finally adjusted by addition of a suitable, biocompatible fluid, preferably WFI. The bulk solution is then filled in vials according to the desired dose.

The freeze-drying is carried out in some embodiments of this invention by using reduced secondary drying times. A preferred protocol involves cooling to a temperature of about −40° C., primary drying at 40 to 80 µbar for 10 to 50 hours, and secondary drying at a lower pressure and at above 0° C. for 10 to 50 hours. In other protocols in the context of this invention cooling to temperatures below −40° C. is performed.

Embodiments of this invention comprise lyophilization by cooling product below −40° C. The primary drying is performed at a temperature from about −20° C. to about −26° C. and a pressure of about 60 µbar for approximately 15 to 40 hours. The secondary drying is carried out at a temperature from about 20° C. to about 30° C. and a pressure of about 100 µbar for approximately 20 to 40 hours.

Embodiments of lyophilised formulations of this invention are suitable for storage at temperatures significantly higher than conventional formulation storage temperatures. Examples of storage temperatures for formulations according to this invention are around +5° C. These temperatures are readily provided by ordinary refrigerators.

DRAWINGS OF THE INVENTION

FIG. 1. Comparative stability study. ET-743 purity evaluation after 6 months storage at 5° C.

Figure 2:
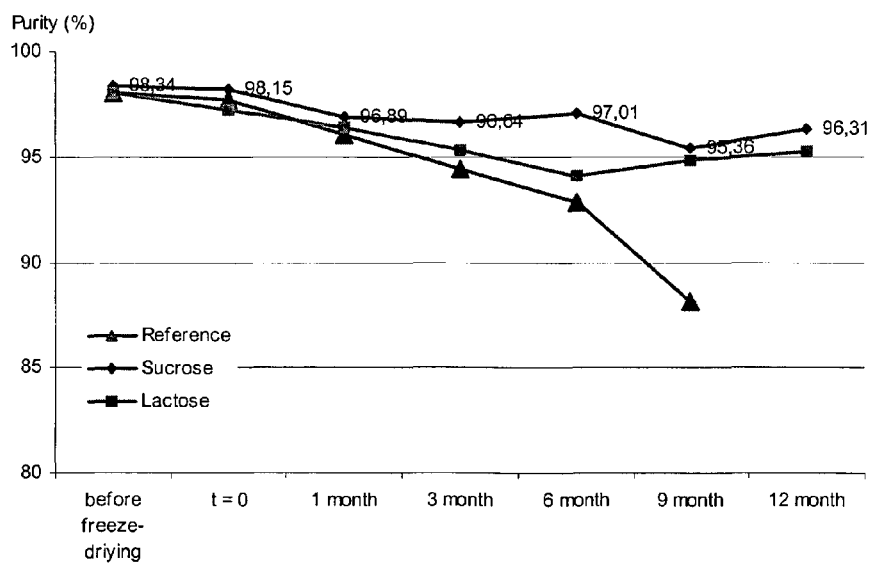

FIG. 2. Comparative stability study. ET-743 purity evaluation after 12 months at 5° C.

Figure 3:
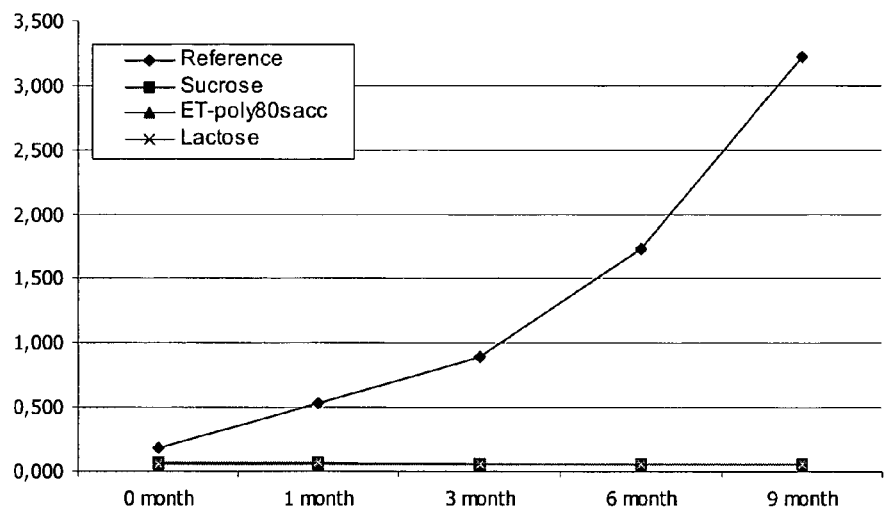

FIG. 3. ET-701 impurity production in different formulations stored during 9 months at 5° C.

Figure 4:
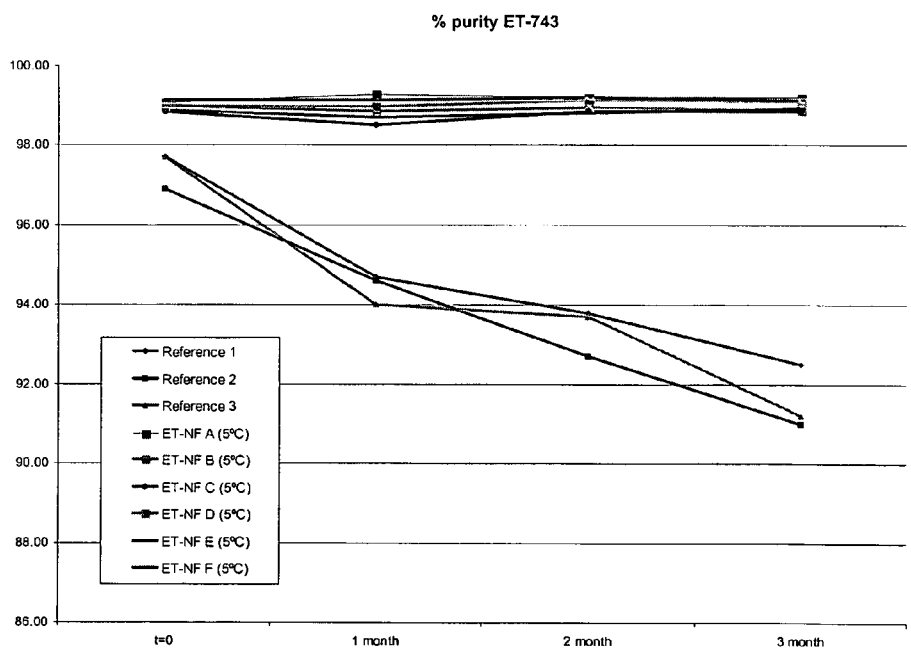

FIG. 4. Comparative ET-743% purity evolution of the new formulations and 3 batches of reference formulation, stored during 3 months at 5° C.

Figure 5:
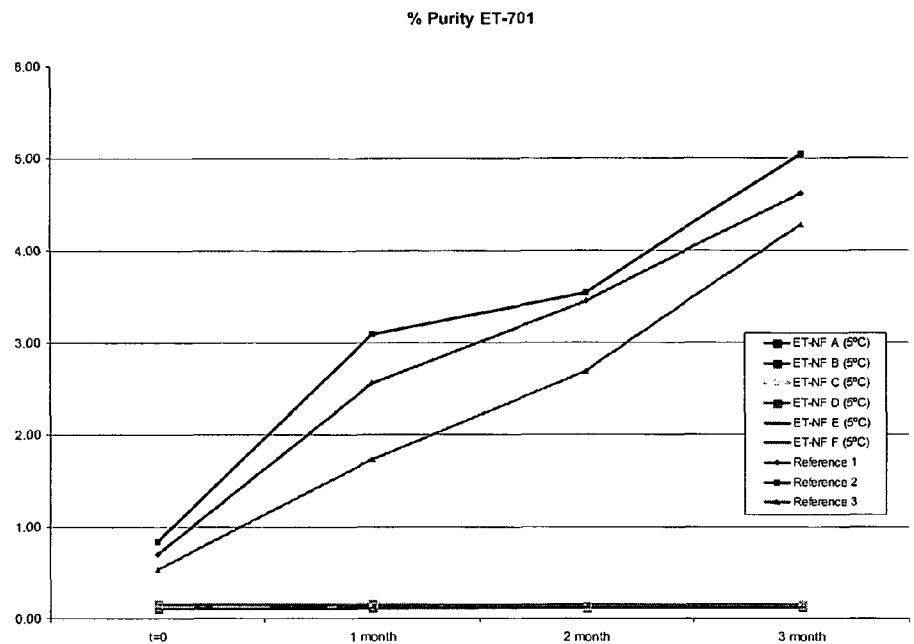

FIG. 5. ET-701 impurity production in different formulations stored during 3 months at 5° C.

Figure 6:
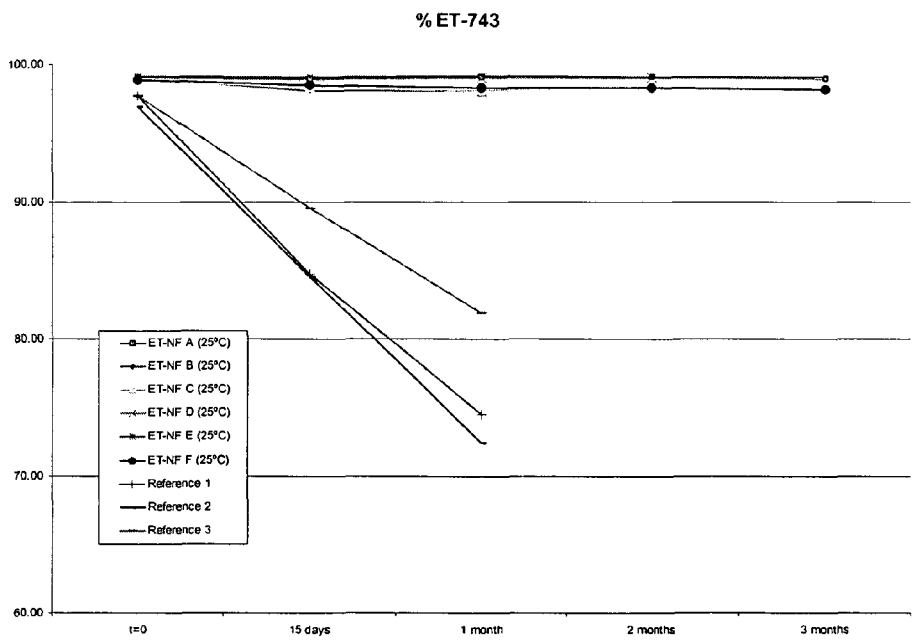

FIG. 6. Comparative ET-743% purity evolution of the new formulations and 3 batches of reference formulation, stored during 3 months at 25° C./65% RH.

Figure 7:
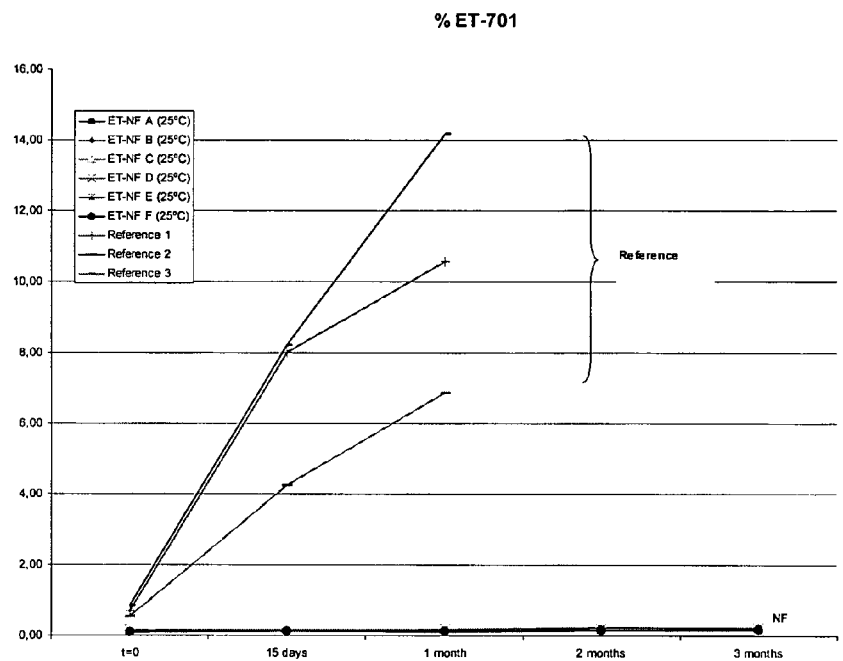

FIG. 7. ET-701 impurity production in different formulations, stored during 3 months at 25° C./65% RH.

Figure 8:
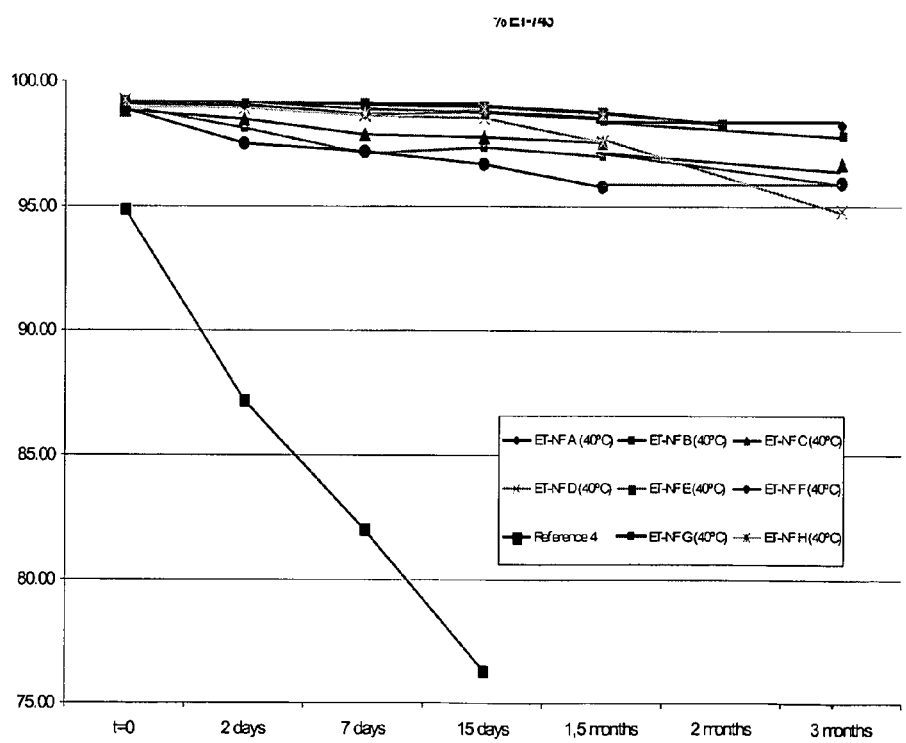

FIG. 8. Comparative ET-743% purity evolution of the new formulations stored at 40° C./70% RH during 3 months.

Figure 9:
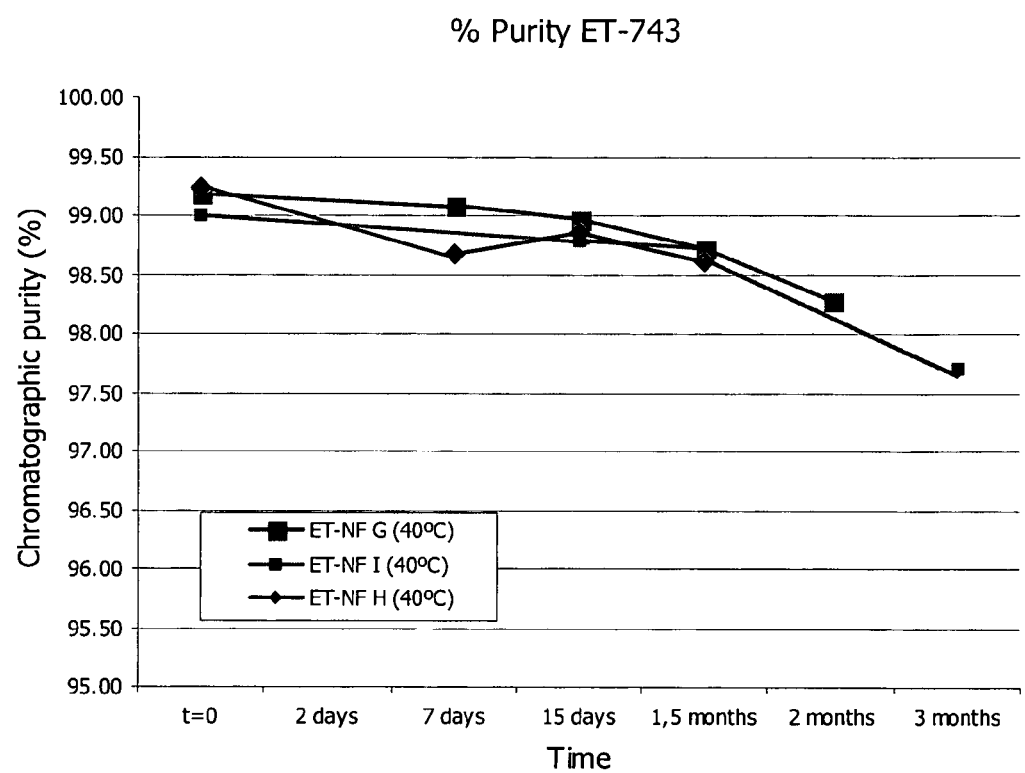

FIG. 9. Comparative ET-743% purity evolution of the new formulations stored at 40° C./70% RH during 3 months.

EXAMPLES

Example 1

This example discloses a comparative stability study of 8 new formulations with the conventional ET-743 formulation (with mannitol). Lactose and sucrose were used to illustrate the present invention. A reference formulation was carried out using mannitol. Other known bulking agents such as dextran (Dextran 40) and povidone (Kollidon 12, PVP) were tried for comparison. Surface-active agents polyoxyl 40 stearate (Myrj 45) or polyoxyethylene 20 sorbitan monooleate (Polysorbate 80) were used in some formulations, and buffer was omitted in some formulations.

Bulk solutions were prepared and freeze-dried by a standardised procedure. A volume of 150 ml of each formulation was prepared:

The amount of potassium phosphate for the final solution (1.02 g) was weighed and dissolved in 90% of final volume (135 ml) of water. Then, the pH was adjusted to pH 4.0 with 0.1N phosphoric acid.

7.85 mg of ET-743 were added to a compounding glass vessel and dissolved by magnetical stirring in ⅔ volume (90 ml) of the potassium phosphate solution for approximately 1 h (dissolution was checked visually).

The amount of bulking agent and surfactant were added and dissolved in ⅓ volume of the potassium phosphate solution. Then, the solution was added to the ET-743 solution and the agitation was maintained for 1 additional hour.

The solution was brought to final weight with water (a density of 1.019 g/cc was adopted for all formulations).

The solution was filtered through a 0.22 μm cellulose filter.

The solution was filled into 25 ml glass vials at 5 ml/vial and maintained at −20° C. until lyophilization process.

Lyophilization was performed according to the following table I:

TABLE I

| Freezing time to −48° C.: | 4 h |
|---|---|
| Primary drying: | 48 h |
| Secondary drying: | 44 h |

After freeze-drying, the vials were sealed. The vials were transferred to a refrigerated area (−20° C.).

The composition for each vial was as follows (Table II), noting that the water evaporates during the freeze-drying procedure.

TABLE II

|  | Reference | Sucrose | Dextran | PVP | Lactose |
|---|---|---|---|---|---|
| ET-743 | 0.250 mg | 0.250 mg | 0.250 mg | 0.250 mg | 0.250 mg |
| Mannitol | 250 mg | | | | |
| Sucrose | | 500 mg | | | |
| Dextran 40 | | | 500 mg | | |
| Kollidon 12 | | | | 375 mg | |
| Lactose | | | | | 500 mg |
| Potassium dihydrogen phosphate | 34 mg | 34 mg | 34 mg | 34 mg | 34 mg |
| Phosphoric acid | q.s. pH 4.0 | q.s. pH 4.0 | q.s. pH 4.0 | q.s. pH 4.0 | q.s. pH 4.0 |
| Water for injection | q.s. 5 ml | q.s. 5 ml | q.s. 5 ml | q.s. 5 ml | q.s. 5 ml |

|  | ET-poly80 | ET-myrj | ET-poly80sacc | ET-p80saccunbuffer |
|---|---|---|---|---|
| ET-743 | 0.250 mg | 0.250 mg | 0.250 mg | 0.250 mg |
| Mannitol | 250 mg | 250 mg | | |
| Sucrose | | | 500 mg | 500 mg |
| Polysorbate 80 | 50 mg | | 50 mg | 50 mg |
| Myrj 45 | | 50 mg | | |
| Potassium dihydrogen phosphate | 34 mg | 34 mg | 34 mg | |
| Phosphoric acid | q.s. pH 4.0 | q.s. pH 4.0 | q.s. pH 4.0 | |
| Water for injection | q.s. 5 ml | q.s. 5 ml | q.s. 5 ml | q.s. 5 ml |

Stability testing was carried at a temperature of 5±3° C.

The purity evaluation of the nine formulations at 5° C. during 3 months is shown in table III and FIG. 1. In the case of the formulations displaying a higher stability (Reference, Sucrose, Lactose and ET-poly80sacc), the stability testing was prolonged until 9 months, and in the case of Lactose and Sucrose formulations the stability testing was even prolonged until 12 months due to their high stability. Data in table III and FIG. 2 show that formulations containing sucrose and lactose displayed an improved stability with a purity decrease of only 2%. This decrease is significantly lower than the decrease observed in the other assayed formulations.

TABLE III

| | ET-743 purity (%) | | | |
|---|---|---|---|---|
| | Reference | Sucrose | Lactose | ET-poly80sacc |
| Before freeze-drying | 98.04 | 98.34 | 98.06 | 97.96 |
| t = 0 | 97.67 | 98.15 | 97.21 | 97.85 |
| 1 month | 96.06 | 96.89 | 96.35 | 97.72 |
| 3 months | 94.37 | 96.64 | 95.33 | 97.58 |
| 6 months | 92.81 | 97.01 | 94.07 | 95.98 |
| 9 months | 88.17 | 95.36 | 94.83 | 96.01 |
| 12 months | | 96.31 | 95.22 | |

| | ET-743 purity (%) | | | | |
|---|---|---|---|---|---|
| | Dextran | PVP | ET-poly80 | ET-myrj | ET-p80saccunbuffer |
| Before freeze-drying | 96.18 | 97.62 | 96.45 | 97.46 | 97.45 |
| t = 0 | 94.64 | 93.72 | 92.46 | 96.36 | 95.80 |
| 1 month | 93.42 | 91.96 | 89.38 | 94.36 | 91.84 |
| 3 months | 84.90 | 90.40 | 81.18 | 85.31 | 88.46 |

As shown in table IV and FIG. 3, the main degradation product of the reference formulation, ET-701, was dramatically reduced when ET-743 was formulated in the presence of sucrose or lactose.

TABLE IV

| | ET-701 (%) | | | |
|---|---|---|---|---|
| | Reference | Sucrose | Lactose | ET-poly80sacc |
| t = 0 | 0.188 | 0.066 | 0.060 | 0.050 |
| 1 month | 0.533 | 0.063 | 0.076 | 0.060 |
| 3 months | 0.890 | 0.057 | 0.054 | 0.050 |
| 6 months | 1.732 | 0.050 | 0.062 | 0.050 |
| 9 months | 3.225 | 0.050 | 0.050 | 0.050 |

It was found in the context of this invention that disaccharides improve the stability of ET-743 in comparison with mannitol. Embodiments of such disaccharides include lactose, sucrose and mixtures thereof. The stability of the formulations comprising disaccharides is also improved in comparison with other formulations containing other conventional bulking agents such as dextran and povidone. Embodiments of disaccharide formulations according to this invention were determined to be stable for at least 12 months at 5° C. Embodiments of formulations according to this invention have impurity content that is significantly reduced with respect to that of conventional formulations. Presence of ET-701 is accordingly reduced. Embodiments of this invention comprise at least one surface-active agent, such as Polysorbate 80. These embodiments exhibited favorable ET-743 solubility properties and stabilization characteristics. The presence of at least one surface-active agent, however, is not a limiting feature of this invention, and other embodiments do not comprise such agent(s).

Example 2

The purpose of this study was to compare the stability of the standard formulation of ET743 with five new formulations. This study evaluated the stability of the formulations at +5° C.

The composition of tested formulations were the following (Table V), noting that the water evaporates during the freeze-drying procedure:

TABLE V

|  | Reference | ETtreal | ETP80treal | ETP80treal 250 | ETP80sacc 250 | ETP80trealgly 250 |
|---|---|---|---|---|---|---|
| ET-743 | 0.250 mg | 0.250 mg | 0.250 mg | 0.250 mg | 0.250 mg | 0.250 mg |
| Mannitol | 250 mg | | | | | |
| Trehalose | | 500 mg | 100 mg | 100 mg | | 200 mg |
| Sucrose | | | | | 100 mg | |
| Polysorbate 80 | | | 10 mg | 10 mg | 10 mg | 150 mg |
| Glycine | | | | | | 15 mg |
| Potassium dihydrogen phosphate | 34 mg | 34 mg | 34 mg | 6.8 mg | 6.8 mg | |
| Phosphoric acid | q.s. pH 4.0 | q.s. pH 4.0 | q.s. pH 4.0 | q.s. pH 4.0 | q.s. pH 4.0 | |
| Hydrochloric acid | | | | | | q.s. pH 4.5 |
| Water for injection | q.s. 5 ml | q.s. 5 ml | q.s. 5 ml | q.s. 1 ml | q.s. 1 ml | q.s. 1 ml |

Bulk solutions were prepared and freeze-dried using the following particular protocols:
Formulations ETtreal, ETP80treal and Reference A weight of 100 g of each formulation was prepared as follows: The amount of potassium phosphate for the final solution was weighed and dissolved in 90% of final volume (90 ml) of water. Then, the pH was adjusted to pH 4.0 with 0.1N phosphoric acid.

The amount of ET-743 (5.0 mg) was added to a compounding glass vessel and dissolved by magnetical stirring in ⅔ volume (60 ml) of the potassium phosphate solution for approximately 1 h (dissolution was checked visually).

The amount of bulking agent and surfactant were added and dissolved in ⅓ volume of the potassium phosphate solution. Then, the solution was added to the ET-743 solution and the agitation was maintained for 1 additional hour.

The solution was brought to final weight with water.

The solution was filtered through a 0.22 μm cellulose filter, taking an aliquot before filtration for IPC.

The solution was filled into 25 ml vials at 5 ml/vial and maintained at −20° C. until the lyophilization process.
Formulations ETP80sacc250, ETP80treal250, ETP80trealgy250

A weight of 30 g of each formulation was prepared as follows:

The amount of potassium phosphate or glycine for the final solution was weighed and dissolved in 90% of final volume (27 ml) of water. Then, the pH was adjusted to pH 4.0 with 0.1N phosphoric acid or 0.1N HCl.

The amount of polysorbate 80 was weighed and added to ⅓ volume of the buffer solution.

The amount of ET-743 (7.5 mg) was added to a compounding glass vessel and dissolved by magnetical stirring in ⅔ volume (60 ml) of the potassium phosphate solution for approximately 1 h (dissolution was checked visually).

The amount of bulking agent was added and dissolved in ⅔ volume of the buffer solution. Then, the solution was added to the ET-743 solution and the agitation was maintained for 10 min.

The solution was brought to final weight with water.

The solution was filtered through a 0.22 μm cellulose filter.

The solution was filled into 10 ml vials at 1 ml/vial and maintained at −20° C. until lyophilization process.

Lyophilization process in all six formulations was performed according to the following table VI:

TABLE VI

| Freezing time to −48° C.: | 2 h 30 min |
|---|---|
| Primary drying: | 29 h |
| Secondary drying: | 36 h |

After freeze-drying, the vials were sealed. The vials were transferred to a refrigerated area (−20° C.).

Stability testing was carried at a temperature of 5±3° C.

All the formulations were more stable at 5° C. than the reference formulation. No major differences were noted between the new formulations. Table VII discloses the ET-743 chromatographic purity of the formulations under study:

TABLE VII

| | ET-743 purity (%) | | | | | |
|---|---|---|---|---|---|---|
| | Reference | ETtreal | ETP80treal | ETP80treal 250 | ETP80sacc 250 | ETP80trealgly 250 |
| Before filtration | 98.63 | 98.30 | 97.10 | 97.67 | 97.22 | 98.3 |
| After filtration | 98.62 | 98.46 | 97.27 | 97.67 | 97.06 | 98.46 |

TABLE VII-continued

| | ET-743 purity (%) | | | | | |
|---|---|---|---|---|---|---|
| | Reference | ETtreal | ETP80treal | ETP80treal 250 | ETP80sacc 250 | ETP80trealgly 250 |
| After freeze-dried | 97.96 | 98.18 | 97.65 | 97.37 | 97.79 | 98.18 |
| 1 month | 97.35 | 98.22 | 97.78 | 96.39 | 97.40 | 98.22 |
| 3 months | 97.65 | 98.53 | 98.25 | 96.61 | 96.66 | 98.53 |
| 6 months | 95.28 | 97.38 | 96.93 | 97.01 | 97.06 | 97.38 |

Example 3

Six formulations ET-NF A, ET-NF B, ET-NF C, ET-NF D, ET-NF E and ET-NF F were manufactured and used for further study of stability at different temperatures.

Sucrose and lactose were selected as bulking agent. Two different buffers were used: sodium citrate buffer 0.1M pH 4 and potassium phosphate 0.05M buffer pH 4. Two different ET-743 concentrations in the bulk solution were tested: 0.250 mg/ml and 0.100 mg/ml. Two different freeze-dried cycles were used depending on the filling volume (4 ml vs 10 ml). A batch of at least 125 vials was manufactured for each formulation.

For each vial the composition of the bulk solution was as follows (Table VIII), noting that the water evaporates during the freeze-drying procedure:

TABLE VIII

| Ingredient | ET-NF A | ET-NF B | ET-NF C | ET-NF D | ET-NF E | ET-NF F |
|---|---|---|---|---|---|---|
| ET-743 | 1 mg | 1 mg | 1 mg | 1 mg | 1 mg | 1 mg |
| Sucrose | 400 mg | — | — | 1000 mg | 1000 mg | — |
| Lactose | — | 400 mg | 1000 mg | — | — | 200 mg |
| Citric acid monohydrate | 43.6 mg | 43.6 mg | 109 mg | 109 mg | — | 43.6 mg |
| Sodium citrate dihydrate | 45.12 mg | 45.12 mg | 112.8 mg | 112.8 mg | — | 45.12 mg |
| Potassium dihydrogen phosphate | — | — | — | — | 68 mg | — |
| Phosphoric acid | — | — | — | — | q.s pH 4 | — |
| Water for injection | 4 ml | 4 ml | 10 ml | 10 ml | 10 ml | 4 ml |

Bulk solutions were prepared and freeze-dried using the following particular protocols:
Formulations ET-NF A, ET-NF B and ET-NF F Preparation of 2 L of citric acid approximately 0.2M: 76.96 g of citric acid were dissolved in a volumetric flask of 2 L and the solution was brought to the final volume with water for injection. The final molarity of the solution of citric acid was 0.183M.

Preparation of 2 L of sodium citrate approximately 0.2M: 117.64 g of sodium citrate were dissolved in a volumetric flask of 2 L and the solution was brought to the final volume with water for injection. The final molarity of the solution of sodium citrate was 0.175M.

Preparation of 4 L of citrate buffer pH 4 approximately 0.1M: 1125 mL of citric acid solution 0.2M were mixed with 875 mL of sodium citrate solution 0.2M in a volumetric flask of 4 L. The solution was brought to the final volume with water for injection. pH of the solution was checked and adjusted to pH 4. The final molarity of the solution of citrate buffer was 0.089M.

143.83 mg of ET-743 was added to a compounding glass vessel and dissolved by magnetical stirring in approximately 80% of required total volume of citrate buffer 0.1 M for approximately 1 h (dissolution was checked visually).

Then, the amount of sucrose or lactose (55 g sucrose formulation A and B, and 27.5 g lactose formulation F) was added and the mixture was stirred for an additional period of approximately 1 h until dissolution.

After checking the pH, the solution was brought to the final volume by adding citrate buffer 0.1 M pH 4. Re-adjusting to pH 4 with citric acid was needed for formulation A. Density of the final solution: 1.04 g/l. Final weight 572 mg.

The solution was filtered through a 0.22 µm PVDF filter.

The solution was filled into 25 ml vials using an automatic pump and silicone platinum-cured tubing 3.2 mm. Standard filling volume was 4 ml. The fill volume was checked at regular intervals (each 15 vials), and fill volume adjusted if required.

After filling lyophilization stoppers were placed and the vials were loaded in the lyophiliser at 5° C.

Lyophilization process was performed according to the following table IX:

TABLE IX

| Cycle | Step | Pressure | Setpoint T (° C.) | Slope (min) | Holding time |
|---|---|---|---|---|---|
| Loading | Shelves T[a] | atm | 5° C. | | |
| Freezing | Freeze 1 | atm | −50° C. | 1 h 50 min 0.5° C./min | |
| | Freeze 2 | atm | −50° C. | | 6 h |
| Vacuum | Ch vacuum | 0.5 mb | | | |
| Sublimation | 1° drying | 0.080 mb | −27° C. | 45 min 0.5° C./min | |
| | 1° drying | 0.080 mb | −27° C. | | 58 h |
| 2nd drying | 2° drying | <0.020 mb | 25° C. | 3 h 30 min 0.25° C./min | |
| | 2° drying | <0.020 mb | 25° C. | | 40 h |
| | stoppering | 0.010 mb | 25° C. | | |

The vials were sealed. A final reconciliation was performed. The vials were transferred to a refrigerated area (−20° C.).

Formulations ET-NF C and ET-NF D

Preparation of 1 L of citric acid approximately 0.2M: 38.48 g of citric acid were dissolved in a volumetric flask of 1 L and the solution was brought to the final volume with water for injection. The final molarity of the solution of citric acid was 0.183 M.

Preparation of 1 L of sodium citrate approximately 0.2M: 58.82 g of sodium citrate were dissolved in a volumetric flask of 1 L and the solution was brought to the final volume with water for injection. The final molarity of the solution of sodium citrate was 0.175 M.

Preparation of 2 L of citrate buffer pH 4 approximately 0.1M: 850 ml of citric acid solution 0.2M were mixed with 650 ml of sodium citrate solution 0.2M in a volumetric flask of 2 L. The solution was brought to the final volume with water for injection. pH of the solution was checked and adjusted to pH 4. The final molarity of the solution of citrate buffer was 0.089 M.

141.21 mg of ET-743 was added to a compounding glass vessel and dissolved by magnetical stirring in approximately 80% of total volume of citrate buffer 0.1 M for approximately 1 h (dissolution was checked visually).

The amount of sucrose or lactose (135 g) was added and the mixture was stirred for an additional period of approximately 1 h until dissolution.

After checking the pH, the solution was brought to the final volume by adding citrate buffer 0.1 M pH 4. No re-adjusting of pH was needed. Density of the final solution: 1.04 g/l. Final weight 1404 mg.

The solution was filtered through a 0.45 µm PVDF filter.

The solution was filled into 25 ml vials using an automatic pump and silicone platinum-cured tubing 3.2 mm. Standard filling volume was 10 ml.

The fill volume was checked at regular intervals (each 15 vials), and fill volume adjusted if required.

After filling lyophilization stoppers were placed and the vials loaded in the lyophiliser at 5° C.

Lyophilization process was performed as before for Formulations ET-NF A, ET-NF B and ET-NF F (Table IX).

Due to the large volume in vials, the cycle proposed failed to give an adequate liophilization and collapse was produced. To avoid a new manufacture, all the vials were reconstituted with 10 ml of purified water, purity profile of some reconstituted solutions was checked, stoppers were replaced for two hole stoppers and the following new cycle was used (Table X):

TABLE X

| Cycle | Step | Pressure | Setpoint T (° C.) | Slope (min) | Holding time |
|---|---|---|---|---|---|
| Vacuum Sublimation | Freeze 2 | atm | −50° C. | | 6 h |
| | Ch vacuum | 0.5 mb | | | |
| | 1° drying | 0.080 mb | −23° C. | 45 min 0.5° C./min | |
| 2$^{nd}$ drying | 1° drying | 0.080 mb | −23° C. | | 80 h |
| | 2° drying | <0.020 mb | 0° C. | 10 h 0.045° C./min | |
| | 2° drying | | 25° C. | 62 h 0.006° C./min | |
| | stoppering | 0.010 mb | 25° C. | | |

After freeze-drying, the vials were sealed. A final reconciliation was performed. The vials were transferred to a refrigerated area (−20° C.).

Formulation ET-NF E 141.21 mg of ET-743 was added to a compounding glass vessel and dissolved by magnetical stirring in 1080 ml wfi+ 3,240 mL phosphoric acid 1N for approximately 1 h (dissolution was checked visually).

The amount of sucrose (135 g) and potassium phosphate (9.18 g) was added and the mixture was stirred for an additional period of approximately 1 h until total dissolution of the molecule.

After checking the pH and re-adjusting to pH 4 with phosphoric acid 1N, the solution was brought to the final volume by adding water for injection. Density of the final solution: 1.04 g/l. Final weight 1404 mg.

The solution was filtered through a 0.45 µm PVDF filter.

The solution was filled into 25 ml vials using an automatic pump and silicone platinum-cured tubing 3.2 mm. Standard filling volume was 10 ml. The fill volume was checked at regular intervals (each 15 vials), and fill volume adjusted if required.

After filling lyophilization stoppers were placed and the vials loaded in the lyophiliser at 5° C.

Lyophilization process was performed as before for Formulations ET-NF A, ET-NF B and ET-NF F (Table 1X).

Due to the large volume in vials, the cycle proposed failed to give an adequate liophilization and collapse was produced. To avoid a new manufacture, all the vials were reconstituted with 10 ml of purified water, purity profile of some reconstituted solutions was checked, stoppers were replaced for two hole stoppers and a new cycle was used as in the case of formulations ET-NF C and ET-NF D (Table X).

After freeze-drying, the vials were sealed. A final reconciliation was performed. The vials were transferred to a refrigerated area (−20° C.).

The desired ET-743 concentration was reached in all cases and the impurity profile was similar between formulations. No differences in ET-743 concentration, and impurity profiles were observed during manufacture (before and after filtration, or after filling). The colour of the bulk solution was slight yellowish in those formulations containing lactose.

Formulations with 4 ml filling or 10 ml filling were initially freeze-dried following the indicated protocol. Whereas formulations with 4 ml filling were correctly lyophilised, formulations with 10 ml filling collapsed. A pressure variation in secondary desiccation indicated collapse and boiling of the freeze-dried cake. Vials of formulations ET-NF C, ET-NF D and ET-NF E were reconstituted with 10 ml of purified water. Purity profile of formulations was checked. As no modification in the purity profile was observed in compare with bulk solutions, it was decided to re-lyophilise the vials using the indicated revised freeze-dried cycle. Batches lyophilised as described, resulted in good aspect without collapse but some bottom contraction.

The ET-743 content of vials was within specifications (95%-105%). Impurities profiles showed similarity between formulations and those profiles are comparable with impurities of bulk solutions. Residual water content was lower or equal than 2% with the largest values being those of formulations of 10 ml filling.

pH of the reconstituted solutions were between pH 4 and pH 4.2 in all cases. Solutions were clear and colourless without visible foreign matter or precipitation. Reconstitution time was similar for all formulations and less than 30 s.

Example 4

The purpose of the study was to investigate the stability of ET-743 in the different formulations ET-NF A, ET-NF B, ET-NF C, ET-NF D, ET-NF E, and ET-NF F at 1 mg/vial under different temperature conditions.

A batch of 130 vials of each formulation ET-NF A, ET-NF B, ET-NF C, ET-NF D, ET-NF E and ET-NF F, 1 mg ET-743/vial, was manufactured according to example 3.

Stability testing was carried at a temperature of 5° C., 25° C./65% RH and 40° C./70% RH.

FIG. 4 and table XI show the ET-743 purity evolution of the new formulations during storage at 5° C., in comparison with three conventional formulations (containing ET-743, mannitol and phosphate buffer).

TABLE XI

| | ET-743 purity (%) | | | | |
|---|---|---|---|---|---|
| | Reference 1 | Reference 2 | Reference 3 | ET-NF A | ET-NF B |
| t = 0 | 97.70 | 96.90 | 97.70 | 99.06 | 99.00 |
| 1 month | 94.70 | 94.60 | 94.00 | 99.28 | 98.86 |
| 2 month | 93.80 | 92.70 | 93.70 | 99.21 | 98.97 |
| 3 month | 92.50 | 91.00 | 91.20 | 99.22 | 98.88 |

| | ET-743 purity (%) | | | |
|---|---|---|---|---|
| | ET-NF C | ET-NF D | ET-NF E | ET-NF F |
| t = 0 | 98.83 | 98.98 | 99.15 | 98.88 |
| 1 month | 98.53 | 99.03 | 99.14 | 98.71 |
| 2 month | 98.88 | 99.15 | 99.21 | 98.80 |
| 3 month | 98.86 | 99.12 | 99.16 | 98.92 |

FIG. 6 and table XII show the ET-743 purity evolution of the new formulations during storage at 25° C./65% RH, in comparison with three conventional formulations (containing ET-743, mannitol and phosphate buffer).

TABLE XII

| | ET-743 purity (%) | | | | |
|---|---|---|---|---|---|
| | Reference 1 | Reference 2 | Reference 3 | ET-NF A | ET-NF B |
| t = 0 | 97.70 | 96.90 | 97.70 | 99.06 | 99.00 |
| 15 days | 84.70 | 84.50 | 89.50 | 98.97 | 98.09 |
| 1 month | 74.50 | 72.40 | 81.90 | 99.08 | 98.13 |
| 2 month | | | | 99.10 | 98.38 |
| 3 month | | | | 98.98 | 98.15 |

| | ET-743 purity (%) | | | |
|---|---|---|---|---|
| | ET-NF C | ET-NF D | ET-NF E | ET-NF F |
| t = 0 | 98.83 | 98.98 | 99.15 | 98.88 |
| 15 days | 98.35 | 98.90 | 99.11 | 98.31 |
| 1 month | 98.01 | 99.03 | 99.13 | 98.32 |
| 2 month | 98.35 | 98.99 | 99.10 | 98.28 |
| 3 month | 98.33 | 98.93 | 99.09 | 98.14 |

FIG. 8 and table XIII show the ET-743 purity evolution of the new formulations during storage at 40° C./70% RH, in comparison with a conventional formulation (containing ET-743, mannitol and phosphate buffer).

TABLE XIII

| | ET-743 purity (%) | | | | | | |
|---|---|---|---|---|---|---|---|
| | Reference 4 | ET-NF A | ET-NF B | ET-NF C | ET-NF D | ET-NF E | ET-NF F |
| t = 0 | 94.92 | 99.06 | 99.00 | 98.83 | 98.98 | 99.15 | 98.88 |
| 2 days | 87.17 | 99.02 | 98.10 | 98.48 | 98.95 | 99.12 | 97.53 |
| 7 days | 82.04 | 98.68 | 97.08 | 97.86 | 98.63 | 98.89 | 97.20 |
| 15 days | 76.33 | 98.75 | 97.33 | 97.77 | 98.55 | 98.71 | 96.66 |
| 1.5 month | | 98.52 | 96.99 | 97.53 | 97.54 | 98.47 | 95.79 |
| 3 month | | 98.24 | 95.92 | 96.67 | 94.79 | 97.84 | 95.91 |

In addition, FIG. 5 and table XIV show the ET-701 impurity production of the new formulations during storage at 5° C., in comparison with three conventional formulations (containing ET-743, mannitol and phosphate buffer).

TABLE XIV

| | ET-701 (%) | | | | |
|---|---|---|---|---|---|
| | Reference 1 | Reference 2 | Reference 3 | ET-NF A | ET-NF B |
| t = 0 | 0.70 | 0.84 | 0.53 | | 0.11 |
| 1 month | 2.56 | 3.09 | 1.73 | | 0.12 |
| 2 month | 3.45 | 3.54 | 2.69 | 0.12 | 0.13 |
| 3 month | 4.61 | 5.04 | 4.28 | 0.13 | 0.13 |

| | ET-701 (%) | | | |
|---|---|---|---|---|
| | ET-NF C | ET-NF D | ET-NF E | ET-NF F |
| t = 0 | 0.15 | 0.16 | 0.15 | 0.11 |
| 1 month | 0.12 | 0.12 | 0.14 | 0.11 |
| 2 month | 0.16 | 0.14 | 0.15 | 0.12 |
| 3 month | 0.16 | 0.15 | 0.15 | 0.12 |

FIG. 7 and table XV show the ET-701 impurity production of the new formulations during storage at 25° C./65% RH, in comparison with three conventional formulations (containing ET-743, mannitol and phosphate buffer).

TABLE XV

| | ET-701 (%) | | | | |
|---|---|---|---|---|---|
| | Reference 1 | Reference 2 | Reference 3 | ET-NF A | ET-NF B |
| t = 0 | 0.70 | 0.84 | 0.53 | 0.09 | 0.11 |
| 15 days | 7.99 | 8.20 | 4.22 | 0.14 | 0.12 |
| 1 month | 10.56 | 14.18 | 6.86 | 0.11 | 0.12 |
| 2 month | | | | 0.15 | 0.16 |
| 3 month | | | | 0.17 | 0.17 |

| | ET-701 (%) | | | |
|---|---|---|---|---|
| | ET-NF C | ET-NF D | ET-NF E | ET-NF F |
| t = 0 | 0.15 | 0.16 | 0.15 | 0.11 |
| 15 days | 0.18 | 0.17 | 0.16 | 0.13 |
| 1 month | | 0.18 | 0.18 | |
| 2 month | 0.18 | 0.19 | 0.24 | 0.15 |
| 3 month | 0.22 | 0.23 | 0.24 | 0.18 |

As shown in these figures, the stability of the new formulations was higher than the stability of the conventional formulations. In addition, the main degradation product of the conventional formulations, ET-701, was dramatically reduced in the new formulations.

Example 5

Three new formulations based on sucrose as bulking agent were used for further stability studies. These new formulations differ in the phosphate buffer molarity (0.05M vs 0.1M) and the filling volume or, in other words, in the ET-743 concentration in the bulk solution (10 ml vs 4 ml).

The manufacture of a batch of at least 50 vials of each of these formulations is described. A summary of formula description per vial is as follows (Table XVI), noting that the water evaporates during the freeze-drying procedure:

TABLE XVI

| Ingredient | ET-NF G Concentration (mg/ml) | ET-NF G Final composition | ET-NF H Concentration (mg/ml) | ET-NF H Final composition | ET-NF I Concentration (mg/ml) | ET-NF I Final composition |
|---|---|---|---|---|---|---|
| ET-743 | 0.250 | 1 mg | 0.100 | 1 mg | 0.250 | 1 mg |
| Sucrose | 100 | 400 mg | 100 | 1 g | 100 | 400 mg |
| Potassium dihydrogen phosphate | 6.8 | 27.2 mg | 13.6 | 136 mg | 13.6 | 54.4 mg |
| Phosphoric acid | q.s to pH 4.0 | q.s pH 4.0 | q.s to pH 4.0 | q.s pH 4.0 | q.s to pH 4.0 | q.s pH 4.0 |
| Water for injection | q.s. to 1 ml | 4 ml | q.s. to 1 ml | 10 ml | q.s. to 1 ml | 4 ml |

A volume of 240 ml for formulations ET-NF-G and ET-NF-I was prepared:

62.76 mg of ET-743 were added to a compounding glass vessel and dissolved by magnetical stirring in a solution of 192 ml wfi+1N phosphoric acid (576 µl for NF G, 816 µl for NF I) for approximately 1 h (dissolution is checked visually).

The amounts of sucrose (24 g) and potassium phosphate (1.63 g for NF G; 3.26 g for NF I) were added and the mixture was stirred for an additional period of approximately 1 h until dissolution.

After checking the pH and re-adjusting to pH 4.00 if necessary with 1N phosphoric acid, the solution was brought to the final volume by adding water for injection. Density of the final solution: 1.04 g/l. Final weight 249.6 g. The solution was filtered through a 0.45 µm PVDF filter.

The solution was filled into 25 ml vials using an automatic pump and silicone platinum-cured tubing 3.2 mm. Standard filling volume was 4 ml.

The fill volume was checked at regular intervals (each 15 vials), and adjusted if required.

After filling lyophilization stoppers were placed and the vials loaded in the lyophiliser at 5° C.

Lyophilization process was performed according to the following parameters (Table XVII):

TABLE XVII

| Cycle | Step | Pressure | Setpoint T (° C.) Slope (min) | Holding time |
|---|---|---|---|---|
| Freezing | Shelves T$^a$ | atm | 5° C. | |
| | Freeze 1 | atm | −50° C. 1 h 50 min 0.5° C./min | |
| | Freeze 2 | atm | −50° C. | 6 h |
| Vacuum Sublimation | Ch vacuum | 0.5 mb | | |
| | 1° drying | 0.080 mb | −27° C. 45 min 0.5° C./min | |
| | 1° drying | 0.080 mb | −27° C. | 58 h |

TABLE XVII-continued

| Cycle | Step | Pressure | Setpoint T (° C.) Slope (min) | Holding time |
|---|---|---|---|---|
| 2$^{nd}$ drying | 2° drying | <0.020 mb | 25° C. 3 h 30 min 0.25° C./min | |
| | 2° drying | | 25° C. | 40 h |
| | 2° drying end | 0.010 mb | 25° C. | |

After freeze-drying, the vials were sealed. A final reconciliation was performed. The vials were transferred to a refrigerated area (−20° C.).

A volume of 600 ml of the formulation ET-NF-H was prepared as follows:

62.76 mg of ET-743 were added to a compounding glass vessel and dissolved by magnetical stirring in a solution of 480 ml wfi+1.44 ml of 1N phosphoric acid for approximately 1 h (dissolution was checked visually).

The amounts of sucrose (60 g) and potassium phosphate (8.16 g) were added and the mixture was stirred for an additional period of approximately 1 h until dissolution.

After checking the pH and re-adjusting to pH 4.00 if necessary with 1N phosphoric acid, the solution was brought to the final volume by adding water for injection. Density of the final solution: 1.04 g/l. Final weight 624 g.

The solution was filtered through a 0.45 µm PVDF filter.

The solution was filled into 25 ml vials using an automatic pump and silicone platinum-cured tubing 3.2 mm. Standard filling volume was 10 ml.

The fill volume was checked at regular intervals (each 15 vials), and adjusted if required.

After filling lyophilization stoppers were placed and the vials loaded in the lyophiliser at 5° C.

Lyophilization process was performed according to the following parameters (Table XVIII):

TABLE XVIII

| Cycle | Step | Pressure | Setpoint T (° C.) Slope (min) | Holding time |
|---|---|---|---|---|
| Freezing | Shelves T$^a$ | atm | 5° C. | |
| | Freeze 1 | atm | −50° C. 1 h 50 min 0.5° C./min | |
| | Freeze 2 | atm | −50° C. | 6 h |
| Vacuum Sublimation | Ch vacuum | 0.5 mb | | |
| | 1° drying | 0.080 mb | −27° C. 45 min 0.5° C./min | |
| | 1° drying | 0.080 mb | −27° C. | 62 h |
| 2$^{nd}$ drying | 2° drying | <0.020 mb | 25° C. 3 h 30 min 0.25° C./min | |
| | 2° drying | | 25° C. | 50 h |
| | 2° drying end | 0.010 mb | 25° C. | |

After freeze-drying, the vials were sealed. A final reconciliation was performed. The vials were transferred to a refrigerated area (−20° C.).

The ET-743 content was within specifications (95%-105%). Impurities profiles showed similarity for all the formulations and comparable with impurities of bulk solutions. Residual water content was lower than 2%, being the highest value for the formulation of 10 ml filling.

The pH of the reconstituted solutions was between pH 4 and pH 4.28 in all cases. Solutions were clear and colourless without visible foreign matter or precipitation. Reconstitution time was similar for all formulations and less than 30 s.

Stability testing was carried during 3 months at a storage temperature of 40° C./70% RH.

FIG. 9 and table XIX show the ET-743 purity evolution of the new formulations during storage at 40° C./70% RH.

TABLE XIX

| | ET-743 purity (%) | | |
|---|---|---|---|
| | ET-NF G | ET-NF H | ET-NF I |
| t = 0 | 99.18 | 99.23 | 99.00 |
| 7 days | 99.04 | 98.68 | |
| 15 days | 98.97 | 98.86 | 98.79 |
| 1.5 month | 98.72 | 98.61 | 98.40 |
| 2 month | 98.29 | | |
| 3 month | | | 97.71 |

In addition, in FIG. 8 the stability data is shown in comparison with a conventional formulation (containing ET-743, mannitol and phosphate buffer).

The results obtained in Examples 4 and 5 indicate that all the formulations comprising a disaccharide as bulking agent are more stable than conventional formulations containing mannitol as bulking agent. Formulation ET-NF-G is a preferred formulation.

Embodiments of formulations according to this invention were tested after storage under a plurality of storage conditions (including temperatures of −20° C., 4° C., and 25° C./60% RH) at various storage times (including storage times of 3 months, 6 months, and 9 months). The assay results indicated that at least 99.5% of ET-743 remained after 9 months of storage at −20° C., at least 99% of ET-743 remained after 9 months of storage at 4° C., and at least 97% of ET-743 remained after 9 months of storage at 25° C./60% RH. Total impurities, including ET-701, ET-745, and other impurities did not exceed 1.66% after 9 months of storage at 25° C./60% RH. In addition, the level of ET-701 impurity did not exceed 0.21% after 9 months of said storage conditions.

All the references cited herein are incorporated by reference in their entirety. The features and advantages of this invention are apparent in light of the disclosure provided herein. Based on this disclosure, modifications and adaptations to various conditions and usages can be made, thus generating embodiments within the scope of this invention.

The invention claimed is:

1. A lyophilised anti-tumor composition comprising a single active anti-tumor compound and a disaccharide selected from sucrose, lactose and a combination thereof, wherein the anti-tumor compound is ET-743 and wherein the disaccharide is present in a sufficient amount to inhibit conversion of the ET-743 into ET-701, such that the ET-743 composition comprises less than 2% ET-701 after storage of the ET-743 composition at 5° C. for 3 months.

2. The lyophilised anti-tumor composition according to claim 1, wherein said disaccharide is lactose.

3. The lyophilised anti-tumor composition according to claim 1, wherein said disaccharide is sucrose.

4. The lyophilised anti-tumor composition according to claim 1, wherein the ratio (w/w) of ET-743 to disaccharide is from about 1:100 to about 1:1500.

5. The lyophilised anti-tumor composition according to claim 4, wherein the ratio (w/w) of ET-743 to disaccharide is from about 1:250 to about 1:600.

6. The lyophilised anti-tumor composition according to claim 5, wherein the ratio (w/w) of ET-743 to disaccharide is about 1:400.

7. The lyophilised anti-tumor composition according to claim 1, which further comprises a buffering agent.

8. The lyophilised anti-tumor composition according to claim 7, wherein said buffering agent is selected from phosphate buffer, citrate buffer, glycine/hydrochloric acid buffer, and mixtures thereof.

9. The lyophilised anti-tumor composition according to claim 1, which further comprises a surface-active agent.

10. The lyophilised anti-tumor composition according to claim 9, wherein the surface-active agent is selected from polyoxyethylene 20 sorbitan monooleate, polyoxyl 40 stearate, and mixtures thereof.

11. The lyophilised anti-tumor composition according to claim 1, wherein the lyophilised formulation is in a vial.

12. The lyophilised anti-tumor composition according to claim 11, wherein ET-743 is present in an amount of about 250 micrograms.

13. The lyophilised anti-tumor composition according to claim 12, wherein said vial contains a composition comprising: about 0.25 mg ET-743, about 100 mg sucrose, and about 6.8 mg potassium dihydrogen phosphate.

14. The lyophilised anti-tumor composition according to claim 11, wherein ET-743 is present in an amount of about 1 mg.

15. The lyophilised anti-tumor composition according to claim 14, wherein said vial contains a formulation comprising: about 1.0 mg ET-743, about 400 mg sucrose, and about 27.2 mg potassium dihydrogen phosphate.

16. A method of making a lyophilised composition of ET-743 according to claim 1, comprising freeze-drying a bulk solution that comprises ET-743 and a disaccharide wherein said disaccharide is selected from sucrose, lactose and a combination thereof.

17. A method of reducing the formation of ET-701 in a composition of ET-743, comprising freeze-drying a bulk solution that comprises ET-743 and a disaccharide to yield a composition according to claim 1 wherein said disaccharide is selected from sucrose, lactose and a combination thereof.

18. A method of preparing a bulk solution for lyophilising to yield a composition according to claim 1, comprising dissolving ET-743 in an acidic medium, mixing the pre-dissolved ET-743 with other components of the bulk solution and, optionally, adjusting the pH of the final solution.

19. A method of preparing a solution for intravenous infusion, comprising: providing a vial that comprises a lyophilised ET-743 composition according to claim 1, adding water to form a reconstituted solution, and diluting said reconstituted solution with an aqueous system.

20. The lyophilised anti-tumor composition according to claim 3, further comprising a buffering agent.

21. The lyophilised anti-tumor composition according to claim 20, further comprising a surface-active agent.

22. A lyophilized anti-tumor composition comprising a single active anti-tumor compound and a disaccharide selected from sucrose, lactose and a combination thereof, wherein the anti-tumor compound is ET-743 and wherein the disaccharide is present in a sufficient amount to inhibit conversion of the ET-743 into ET-701, such that the ET-743 composition comprises less than 2% ET-701 after storage of the ET-743 composition at 25° C. for 3 months.

23. The lyophilised anti-tumor composition according to claim 22, wherein the lyophilised composition is in a vial.

24. The lyophilised anti-tumor composition according to claim 22, wherein the disaccharide is sucrose.

25. The lyophilised anti-tumor composition according to claim 22, wherein the disaccharide is lactose.

26. The lyophilised anti-tumor composition according to claim 22, further comprising a buffer.

* * * * *